United States Patent
Syamakumari et al.

(10) Patent No.: US 9,915,669 B2
(45) Date of Patent: Mar. 13, 2018

(54) WATER SOLUBLE POLYFLUORENE FUNCTIONALIZED WITH GLUCURONIC ACID USEFUL IN BILIRUBIN SENSING

(71) Applicant: COUNCIL OF SCIENTIFIC & INDUSTRIAL RESEARCH, New Delhi (IN)

(72) Inventors: Asha Syamakumari, Pune (IN); Senthil Kumar, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 53 days.

(21) Appl. No.: 14/908,482

(22) PCT Filed: Jul. 31, 2014

(86) PCT No.: PCT/IN2014/000505
§ 371 (c)(1),
(2) Date: Jan. 28, 2016

(87) PCT Pub. No.: WO2015/015517
PCT Pub. Date: Feb. 5, 2015

(65) Prior Publication Data
US 2016/0169917 A1 Jun. 16, 2016

(30) Foreign Application Priority Data
Jul. 31, 2013 (IN) .............. 2293/DEL/2013

(51) Int. Cl.
*G01N 33/72* (2006.01)
*C07H 19/056* (2006.01)
*G01N 33/58* (2006.01)

(52) U.S. Cl.
CPC ......... *G01N 33/728* (2013.01); *C07H 19/056* (2013.01); *G01N 33/582* (2013.01);
(Continued)

(58) Field of Classification Search
CPC .... G01N 33/728; G01N 33/72; G01N 33/528; Y10T 436/146666; Y10T 436/103332; C07H 19/056
(Continued)

(56) References Cited

U.S. PATENT DOCUMENTS

| | | | |
|---|---|---|---|
| 3,814,586 A | 6/1974 | Fraser, Jr. et al. | |
| 4,612,290 A | 9/1986 | Yazawa et al. | |

OTHER PUBLICATIONS

Kan-Yi Pu, Jianbing Shi, Lihua Wang, Liping Cai, Guan Wang, and Bin Liu "Mannose-Substituted Conjugated Polyelectrolyte and Oligomer as an Intelligent Energy Transfer Pair for Label-Free Visual Detection of Concanavalin A" Macromolecules 2010, 43, 9690-9697.*

(Continued)

*Primary Examiner* — Christine T Mui
*Assistant Examiner* — Emily R. Berkeley
(74) *Attorney, Agent, or Firm* — Maschoff Brennan

(57) ABSTRACT

The present invention provide water soluble polyfluorenes functionalized with glucuronic acid useful in sensing bilirubin in aqueous medium and process for preparation thereof.
The invention further deals with detecting bilirubin in human serum samples in the range from normal (<25 μmol/L~1.2 mg/dL) human bilirubin level to jaundiced bilirubin level (>50 μmol/L~2.5 mg/dL).[1] This is a fluorescence turn-off mode of detection where blue fluorescence of polymer quenches and becomes colorless. The water soluble polyfluorenes functionalized with glucuronic acid can detect free bilirubin in the range from $1\times10^{-4}$ M to $1\times10^{-7}$ M moles in aqueous and buffer media as a change in the fluorescence signal.

7 Claims, 10 Drawing Sheets

(52) U.S. Cl.
CPC ..... *G01N 33/72* (2013.01); *Y10T 436/103332* (2015.01); *Y10T 436/146666* (2015.01)

(58) Field of Classification Search
USPC .................................................. 436/97, 12
See application file for complete search history.

(56) References Cited

OTHER PUBLICATIONS

Qi Chen, Yi Cui, Tian-Long Zhang, Jie Cao, and Bao-Hang Han "Fluorescent Conjugated Polyfluorene with Pendant Lactopyranosyl Ligands for Studies of Ca2+-Mediated Carbohydrate-Carbohydrate Interaction" Biomacromolecules 2010, 11, 13-19.*

Ryan M. Walczak, Robert N. Brookins, Alice M. Savage, Eveline M. van der Aa, and John R. Reynolds "Convenient Synthesis of Functional Polyfluorenes via a Modified One-Pot Suzuki-Miyaura Condensation Reaction" Macromolecules 2009, 42, 1445-1447.*

"Self-Assembly in Tailor-Made Polyfluorenes: Synergistic Effect of Porous Spherical Morphology and FRET for Visual Sensing of Bilirubin" T. Senthilkumar and S. K. Asha, Macromolecules 46(6) pp. 2459-2171, 2013.

"Detection and measurement of total bilirubin in serum, with use of surfactants as solubilizing agents" Clinical Chemistry, 20(4), 447-53 F. C. Pearlman, et al, 1974.

"Ionic, Water-Soluble Polyfluorene-Type Copolymers" by Swapna Pradha, Oct. 2004.

"Fluorescent Nanoparticles Comprising Amphiphilic Roc-Col Graft Copolymers" Macromolecules, vol. 41, No. 4 Jun Hong Yao et al, Feb. 1, 2008.

J.B. Landis and H.L. Pardue, "Kinetics of the reactions of unconjugated and conjugated bilirubins with p-diazobenzenesulfonic acid" Clinical Chemistry, 24 (10), 1690-1699, 1978.

* cited by examiner

Fig: 1

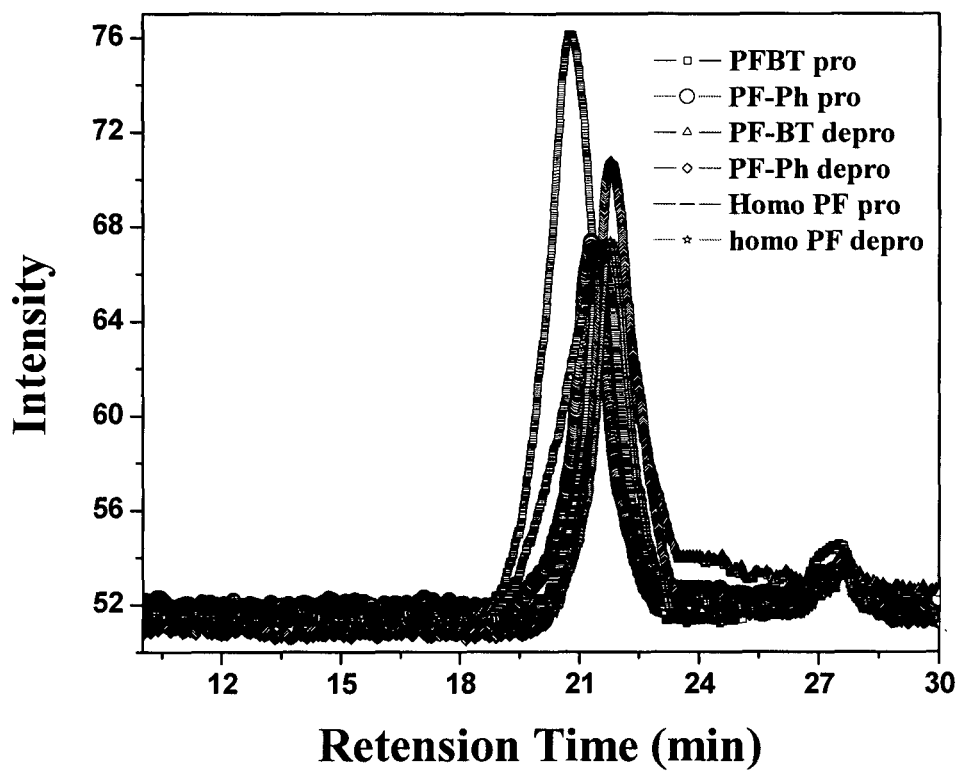
Fig: 7

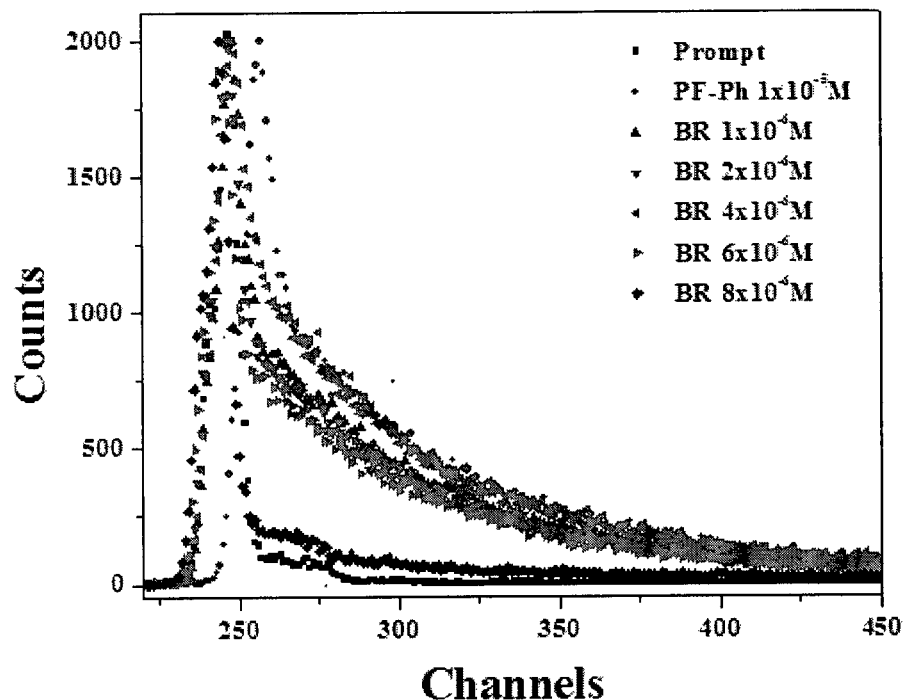
Fig: 8
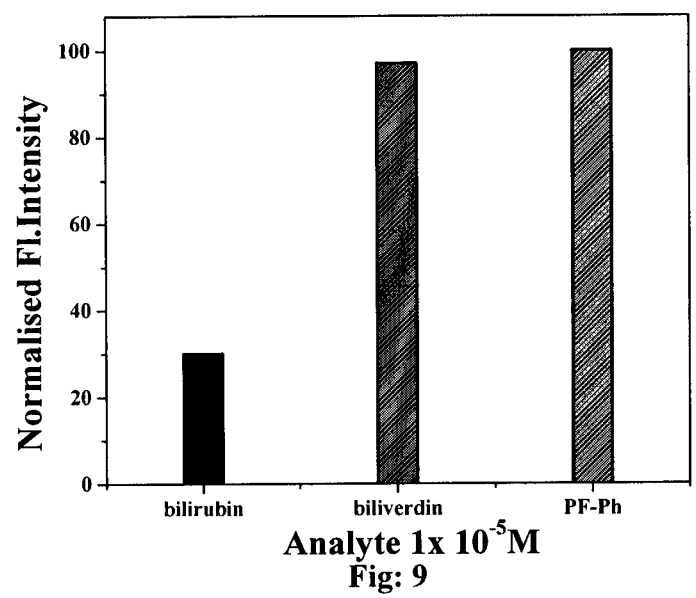
Fig: 9

WATER SOLUBLE POLYFLUORENE FUNCTIONALIZED WITH GLUCURONIC ACID USEFUL IN BILIRUBIN SENSING

FIELD OF THE INVENTION

The present invention relates to water soluble polyfluorenes functionalized with glucuronic acid useful in sensing bilirubin in aqueous medium. Particularly, the present invention relates to process for the preparation of water soluble polyfluorenes functionalized with glucuronic acid. More particularly, the invention relates to detecting bilirubin in human serum samples in the range from normal (<25 µmol/L~1.2 mg/dL) human bilirubin level to jaundiced bilirubin level (>50 µmol/L~2.5 mg/dL). This is a fluorescence turn-off mode of detection where blue fluorescence of polymer quenches and becomes colorless. The water soluble polyfluorenes functionalized with glucuronic acid can detect free bilirubin in the range from $1 \times 10^{-4}$ M to $1 \times 10^{-7}$ M moles in aqueous and buffer media as a change in the fluorescence signal.

BACKGROUND AND PRIOR ART OF THE INVENTION

Bilirubin is a breakdown product of hemoglobin which is an oxygen carrier in blood. In human body bilirubin is present in two forms. Indirect or unconjugated bilirubin (insoluble in water) is present as free bilirubin that circulates in the plasma and is taken up by liver cells where it is enzymatically esterified with glucuronic acid to form conjugated or direct bilirubin. Conjugated bilirubin is water soluble and is easily excreted through bile. The normal levels of bilirubin in human blood is as follows; direct bilirubin in the range of 0 to 0.3 mg/dl and total bilirubin should be 0.3 to 1.9 mg/dl. Abnormal levels of total bilirubin (conjugated and unconjugated) detected in serum samples is an indicator for disturbed bilirubin metabolism. Determination of the amount of bilirubin in body fluid, especially in blood, is important factor for detection of haemolysis and for checking liver function. The excess or over production or problem in bilirubin metabolism leads to jaundice, liver disorders etc. Therefore, detecting bilirubin levels in the body is very important to regulate our body. Diazotization is one of the most common methods of determination, wherein, bilirubin is coupled with diazonium salt such as diazosulfanilic acid and the amount of the resulting colorant is measured in a spectrophotometer to estimate the bilirubin content in the sample. Details of the diazotization method are described in J. B. Landis and R L. Prude, Clinical Chemistry, 24 (10), 1690-1699 (1978). However, this method has its own disadvantage as it take lots of time for total color development and also overestimates the amount of conjugated bilirubin.

U.S. Pat. No. 4,612,290 discloses a method for quantitative determination of bilirubin which comprises bringing a bilirubin-containing aqueous liquid sample into contact with a hydrophobic bilirubin extracting composition containing a hydrophobic amine capable of extracting bilirubin. The amine extracts the bilirubin in said aqueous liquid sample. Photometry is then used to determine the concentration of bilirubin extracted with the bilirubin extracting composition.

Article titled "Self-Assembly in Tailor-Made Polyfluorenes: Synergistic Effect of Porous Spherical Morphology and FRET for Visual Sensing of Bilirubin" by T. Senthilkumar and S. K. Asha published in Macromolecules, 2013, 46 (6), pp 2159-2171 reports two new fluorene-based homo- (PDP-PF) and copolymers (PDPPF-co-Ph) were synthesized with a bulky 3-pentadecylphenoxy (PDP) group appended hexyl chains at the 9, 9' position using Suzuki coupling polymerization. Also the sensing efficiency of both polymers toward the biologically important analyte bilirubin was demonstrated in organic medium by the quenching of polymer fluorescence and FRET-based bilirubin emission.

Article titled "Detection and measurement of total bilirubin in serum, with use of surfactants as solubilizing agents" published in Clinical Chemistry, 1974; 20(4), 447-53 reports a new method for measuring total bilirubin in serum. Nonionic, cationic, or anionic surfactants can be used as solubilizing agents to promote the diazo coupling of indirect-reacting bilirubin.

Dissertation titled" Ionic, Water-Soluble Polyfluorene-Type Copolymers" by swapna Pradhan reports the synthesis of 2,7-dibromo-9,9-bis(6-bromohexyl)fluorene and Synthesis of poly {9,9-bis[6-(N,N-dimethylamino)hexyl]fluoreneco-1,4-phenylene}. The report also illustrated the conjugated copolymers based on alternating fluorene and phenylene building blocks are also promising efficient and stable blue luminescent materials.

In spite of the above and other existing methods, sensing bilirubin is a very challenging task because of its less solubility, poor emission property and poor quantum yield in water as well as in common organic solvents. Conjugated polymers are used in chemo and biosensors and they can be structurally modified to improve water solubility, good emission and high quantum yield. For the present invention polyfluorene was functionalized with glucuronic acid which made it water soluble. Glucuronic acid is known for its ability for selective interaction with bilirubin. Thus, functionalizing polyfluorene with glucuronic acid has the added advantage of introducing secondary interactions between bilirubin and glucuronic acid, which is expected to bring the polymer and bilirubin closer for better and more efficient fluorescence sensing response.

The delocalised π electrons in conjugated polymers are sensitive even to minor perturbations resulting in amplified signal response due to which they find applications as chemical and biosensors. By taking advantage of overlapping photophysical properties of bilirubin and polyfluorenes the inventors have developed a model polyfluorene sensor to detect unconjugated bilirubin via FRET process for the first time. A few attempts have been reported in literature for the sensing of bilirubin in aqueous medium via the fluorescence technique. However, despite the best efforts, sensing of bilirubin in water is very difficult, due to poor solubility, reactivity and very low quantum yield of bilirubin emission. The other challenge is the selectivity in the sensing processes.

Therefore, designing and synthesizing a fluorescence sensor with high selectivity, and detecting the bilirubin in aqueous medium is desired.

OBJECT OF THE INVENTION

Main object of the present invention is to provide water soluble polyfluorene functionalized with glucuronic acid which is useful for sensing bilirubin in aqueous medium, buffer, and human serum samples.

Another object of the present invention is to provide a process for synthesis of water soluble polyfluorene functionalized with glucuronic acid.

Yet another object of the present invention is to provide a free bilirubin sensing and concentration determination protocol by fluorescence technique in the range of $1\times10^{-4}$ M to $1\times10^{-7}$ M.

Yet another objective of the present invention is to detect free bilirubin in human serum samples. Normal and jaundiced patient samples can be differentiated by the present detection methods.

SUMMARY OF THE INVENTION

Accordingly, present invention provides a compound of formula (I)

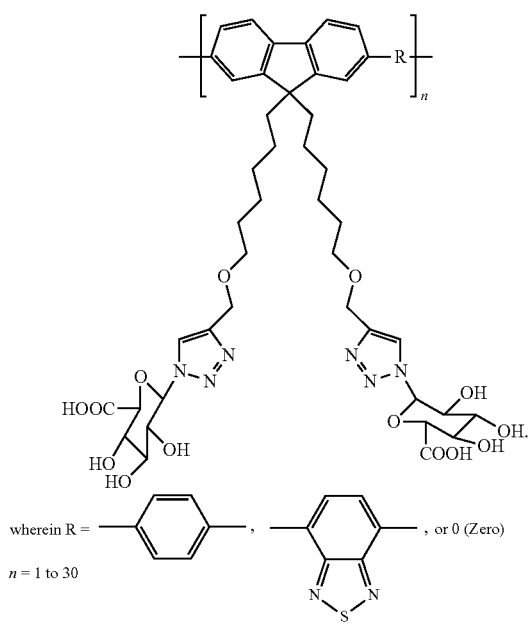

In an embodiment of the present invention, the compounds are water soluble.

In another embodiment of the present invention, the compounds are useful for sensing bilirubin in aqueous medium by fluorescence in the range of $1\times10^{-4}$ M to $1\times10^{-7}$ M micro moles.

In yet another embodiment of the present invention, the compounds are useful for detecting bilirubin in human serum samples in the range from normal (<25 μmol/L~1.2 mg/dL) human bilirubin level to jaundiced bilirubin level (>50 μmol/L~2.5 mg/dL).[1]

In yet another embodiment, present invention provides a process for the preparation of compound of formula I comprising the steps of:
a) refluxing the reaction mixture of 2, 7-dibromofluorene and 1, 6-dibromo-hexane in presence of NaH in THF for period in the range of 10 to 12 hr followed by extraction to get 2, 7 dibromo-9, 9-(6-bromohexyl) fluorene;
b) etherifying the 2, 7 dibromo-9, 9-(6-bromohexyl) fluorene as obtained in step (a) with propargyl alcohol to give 2, 7-dibromo-9, 9-bis (6-(prop-2-yn-1-yloxy) hexyl)-9H-fluorene;
c) protecting D-Glucuronic acid with acetic anhydride to give penta acetylated product;
d) refluxing the penta acetate product as obtained in step (c) with methanol to give 6-(methoxy-carbonyl) tetrahydro-2H-pyran-2, 3, 4, 5-tetrayl tetraacetate;
e) reacting 6-(methoxy-carbonyl) tetrahydro-2H-pyran-2, 3, 4, 5-tetrayl tetraacetate as obtained in step (d) with TMS-$N_3$ and $SnCl_4$ followed by purification by column chromatography to obtain 2-azido-6-(methoxy-carbonyl) tetrahydro-2H-pyran-3,4,5-triyltriacetate;
f) reacting compound of step (b) and compound of step (e) to get the sugar functionalized fluorene monomer;
g) polymerizing the compound of step (f) by suzuki coupling to get glucuronic acid functionalized polyfluorene;
h) stirring the glucuronic acid functionalized polyfluorene in methanol and dichloromethane, $CH_3ONa$ in methanol solution at temperature in the range of 25 to 30° C. for period in the range of 5 to 6 hrs followed by hydrolyzing the ester using dilute HCl for period in the range of 20 to 24 h, purifying by dialysis to give water soluble compound of formula I.

In yet another embodiment of the present invention, the suzuki coupling in step (g) is carried out by refluxing the monomer with phenyl 1, 4-diboronic ester in presence of $K_2CO_3$ and THF for 36 hrs under nitrogen atmosphere.

In yet another embodiment of the present invention, the click reaction is carried out in step (f) for 24 hrs in argon atmosphere.

In yet another embodiment, present invention provides a process for determining free bilirubin content within an aqueous medium comprising the steps of:
a) preparing bilirubin stock solution in water or buffer at pH=10 by the addition of NaOH;
b) titrating polyfluorene functionalized with glucuronic acid polymeric solution in distilled water or buffer with bilirubin;
c) determining by fluorimetry, quenching of fluorescence intensity at 420 nm.

In yet another embodiment of the present invention, the stock solution concentration ranges from $1\times10^{-4}$ M to $1\times10^{-7}$ M.

In yet another embodiment, present invention provides use of polyfluorene functionalized with glucuronic acid for determination of free bilirubin content within an aqueous medium.

In yet another embodiment, present invention provides use of polyfluorene functionalized with glucuronic acid, wherein polyfluorene functionalized with glucuronic acid compounds are water soluble.

BRIEF DESCRIPTION OF THE DRAWINGS

FIG. 7 shows gel permeation chromatography diagram to determine the molecular weight of the polymers carried out in DMF as solvent.

FIG. 8 shows of Fluorescence life time decay studies for PF-Ph.

FIG. 9 shows quenching towards bilirubin not to biliverdin by PF-Ph polymer.

DETAILED DESCRIPTION OF THE INVENTION

Figure 1:
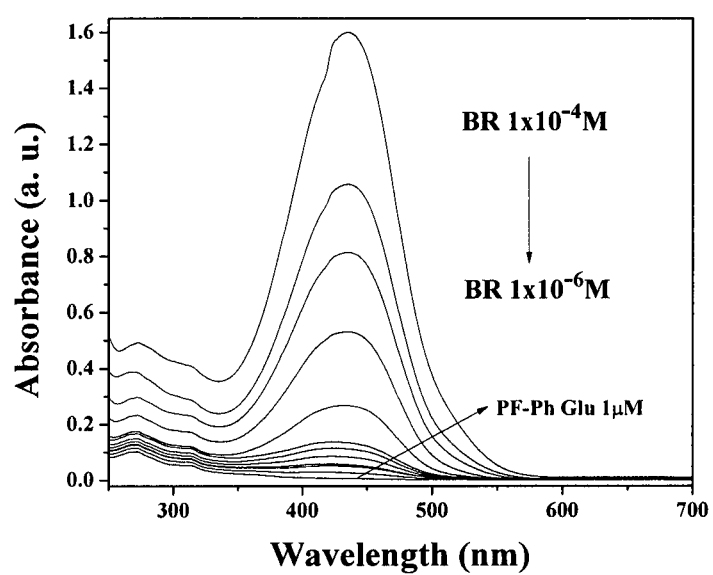
FIG. 1 shows absorption spectra of the PF-Ph-Glu polymer upon various additions of bilirubin (concentration range from $1\times10^{-6}$ M to $1\times10^{-4}$ M in PBS buffer at pH=10).

The present invention provides a water soluble polyfluorene functionalized with glucuronic acid of formula (I) which are useful for sensing bilirubinin in aqueous medium.

Formula (I)

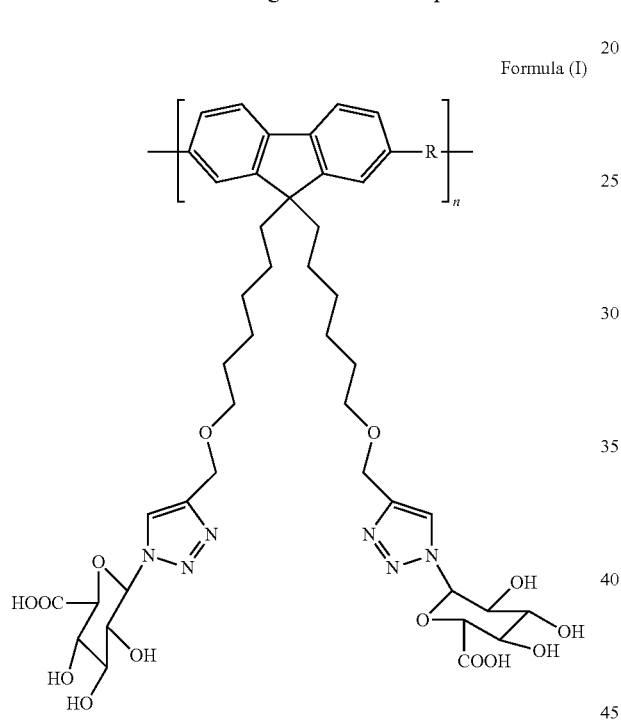

Wherein R=

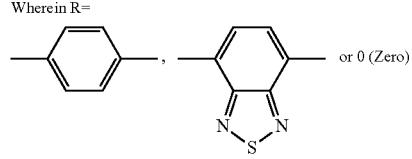

when R is Phenyl, formula I indicates polyfluorene-alt-phenyl copolymer, when R is benzothiadiazole it is polyfluorene-alt-benzothiadiazole polymer and when R is 0 it is homopolymer, and n is 1 to 30.

The compound of formula (I) are selected from the group consisting of

Compound 1

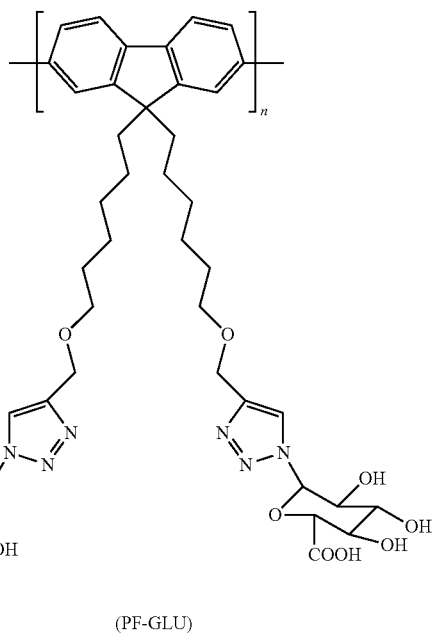

(PF-GLU)

Compound 2

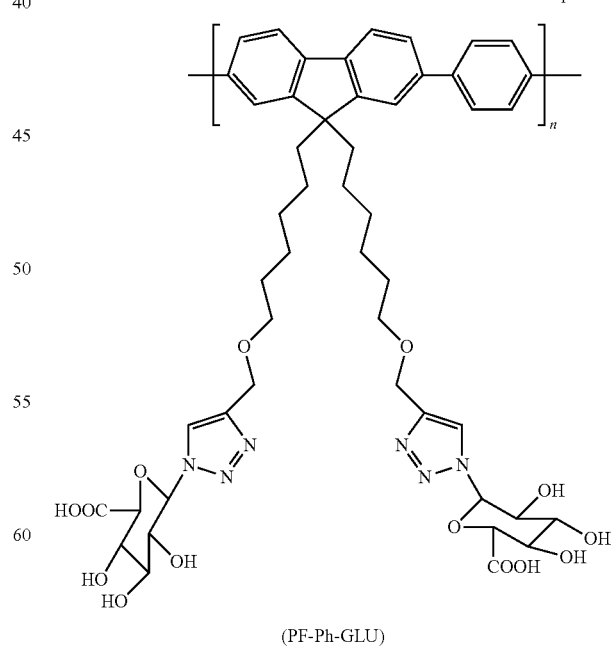

(PF-Ph-GLU)

Compound 3

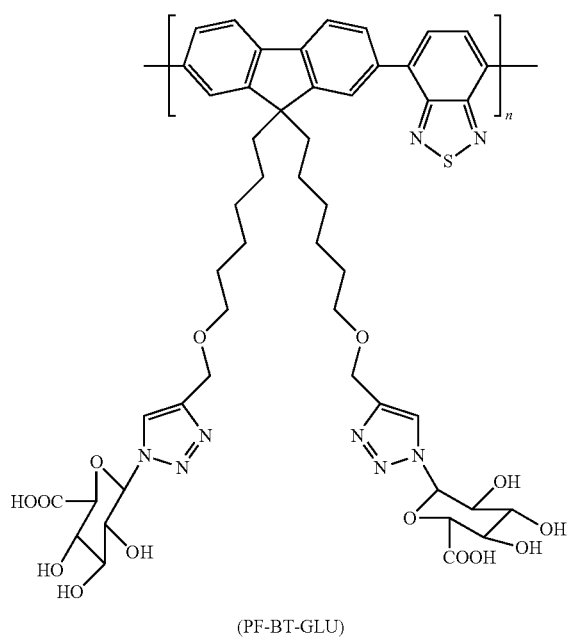

(PF-BT-GLU)

The functionalized polyfluorenes show specific noncovalent interactions and also having their emission spectra matching with the absorption spectra of bilirubin thereby allowing for fluorescence resonance energy transfer (FRET) from polymer to bilirubin, which result in the quenching of emission of the polyfluorene with simultaneous weak emission from bilirubin. Thus a fluorescent turn-off/color change based sensing of bilirubin is achieved.

However, polyfluorenes are not soluble in water or in aqueous medium in which the sensing of bilirubin is preferred. Therefore, the invention further provides functionalization of polyfluorene backbone with Glucuronic acid for the selective sensing of bilirubin in aqueous medium. The glucoronic acid not only results in selective interaction with bilirubin, but also it makes the polyfluorene water soluble. This water soluble polyfluorenes have been used in the present invention to sense the bilirubin via fluorescence quenching in aqueous medium with pronounced selectivity and sensitivity.

The water soluble polyfluorene functionalized with glucuronic acid of formula (I) are synthesized by functionalizing the fluorene compounds with glucuronic acid followed by polymerizing the same to obtain water soluble polyfluorene functionalized with glucuronic acid that can be used to sense the level of bilirubin in aqueous media.

The synthesis of polymers is generally accomplished by the activation of methylene bridges of the fluorene unit and further sugar unit is attached via the click reaction to the monomers of desired functionality. Homo and copolymerization of the monomer was done with using diboronic esters to give corresponding homopolymer and 2 different copolymers.

A process for the synthesis of polyfluorene functionalized with glucuronic acid comprising the following steps:
a) Refluxing at 65° C. the mixture of 2, 7-dibromofluorene and 1, 6-dibromohexane in presence of NaH in THF for 12 hrs followed by extraction with solvent to get 2, 7 dibromo-9, 9-(6-bromohexyl) fluorene.
b) Etherified the compound of step (a) with propargyl alcohol to give 2, 7-dibromo-9, 9-bis (6-(prop-2-yn-1-yloxy) hexyl)-9H-fluorene.
c) Protecting D-Glucuronic acid with acetic anhydride to give penta acetylated product.
d) Refluxing the penta acetate product of step (c) with methanol to give 1, 2, 3, 4-Tetra-O-Acetyl-methyl-β-D-Glucuronide.
e) Reacting compound of step (d) with TMS-N₃ and SnCl₄ gave azide as major product followed by purification by column chromatography to get 2, 3, 4-tri-O-acetyl-1-azido-1-deoxy-β-D-glucuronic acid methyl ester.
f) Reacting compound of step (b) and compound of step (e) by click chemistry to get the sugar functionalized fluorene monomer.
g) Polymerizing the compound of step (f) by Suzuki coupling to get polyfluorene functionalized with glucuronic acid.
h) Stirring the glucuronic acid functionalized polymer in methanol (6 mL) and dichloromethane (10 mL), CH₃ONa in methanol solution (3 mL, 1 M) at room temperature for 8 hrs followed by treating with dilute HCl and purified by dialysis.

Step wise reaction scheme of synthesis for the polymers is shown below:

Step-1: Synthesis of azide functionalized glucuronic acid methyl ester

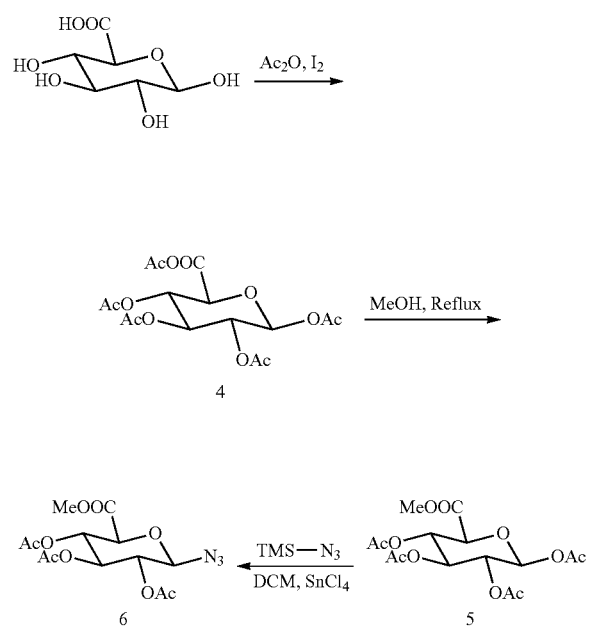

Step-2: Synthesis of propargyl functionalized fluorene

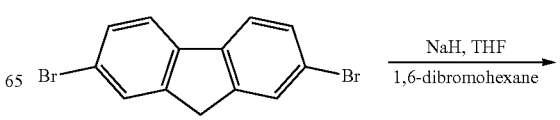

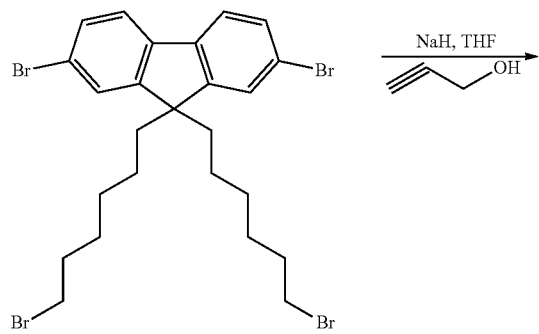
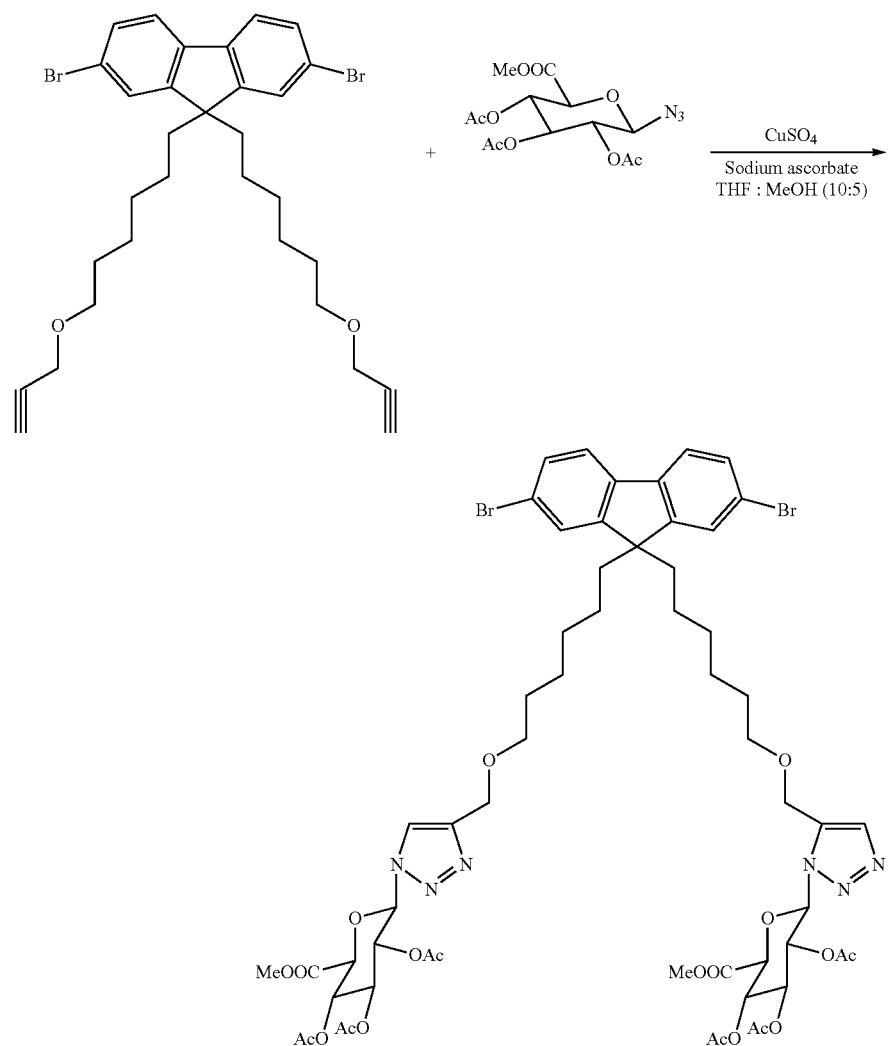
Step-3: Synthesis of glucuronic acid functionalized fluorine monomer 11
-continued
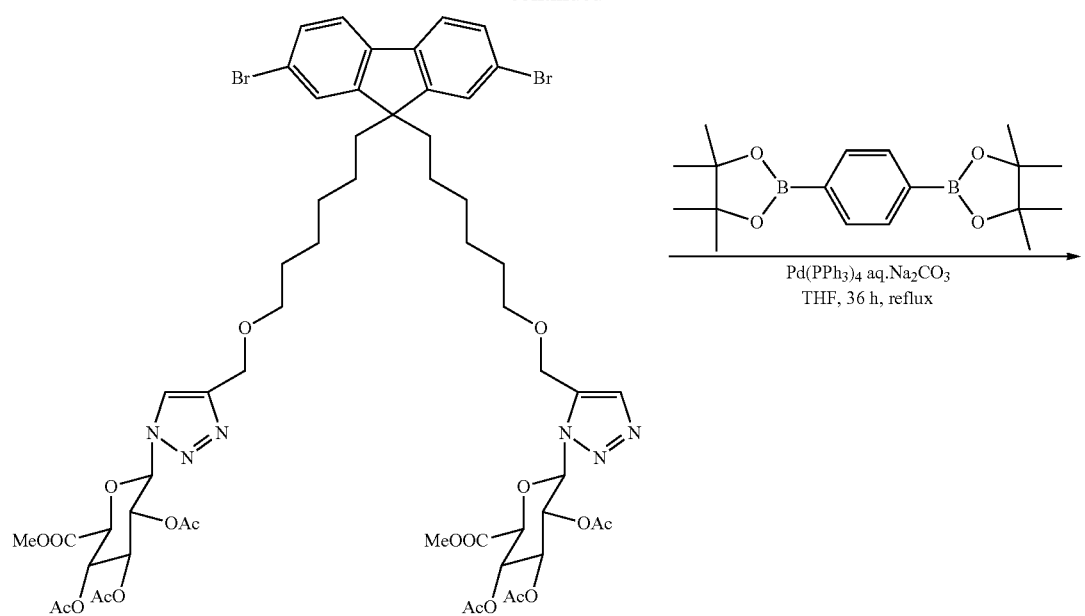
12
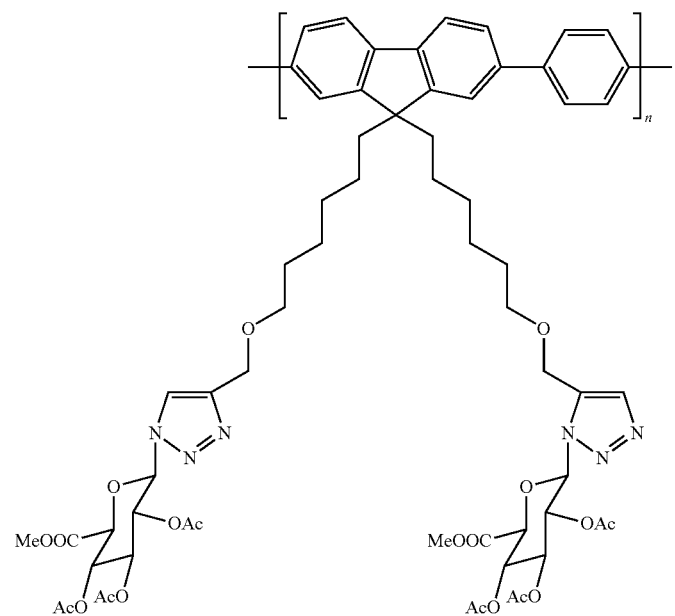

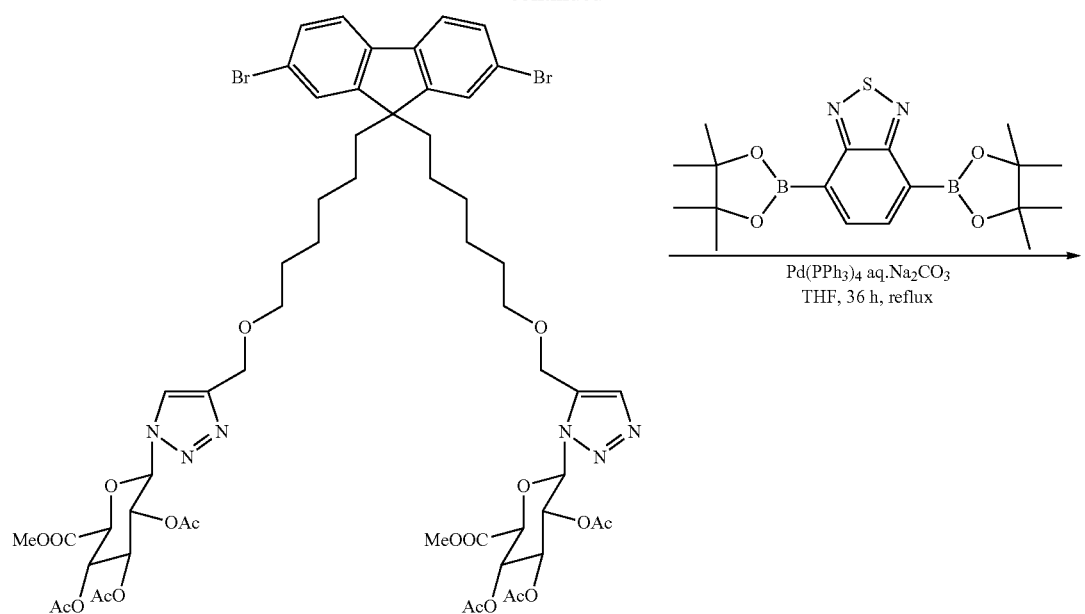
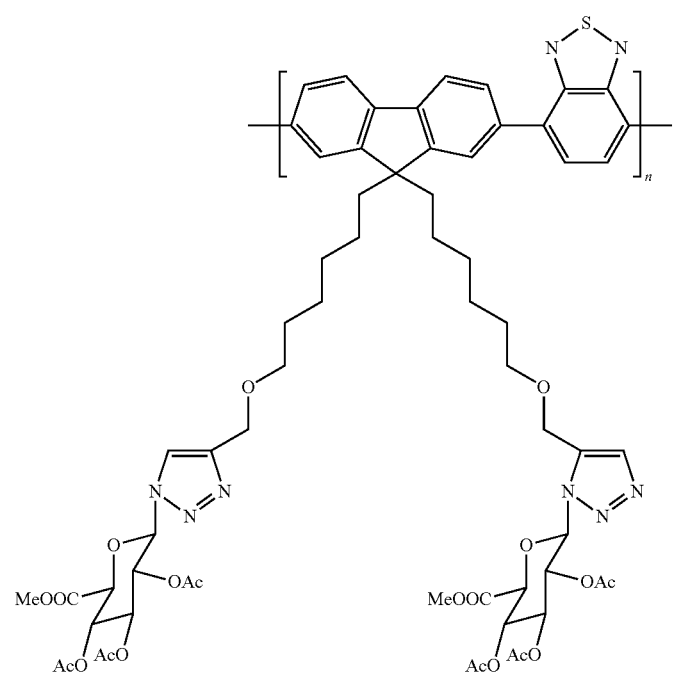

-continued
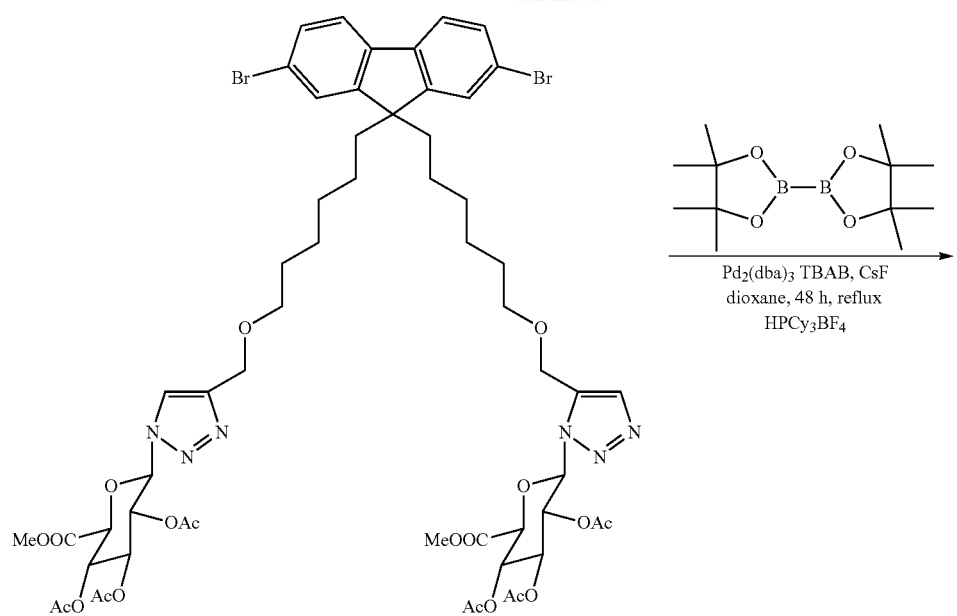
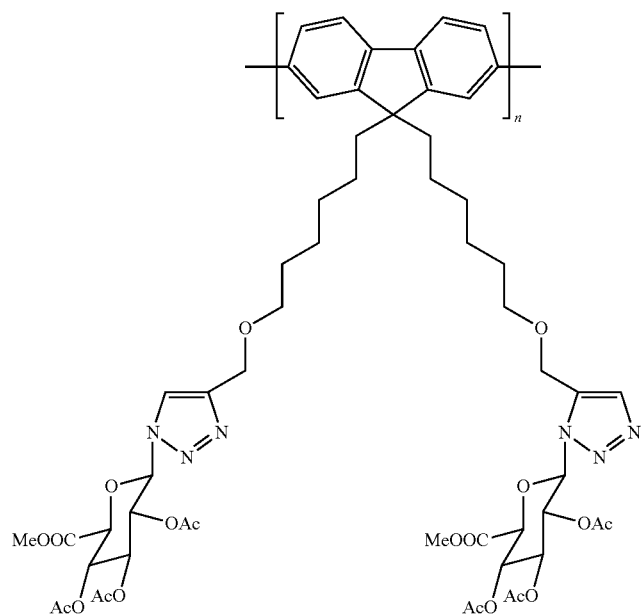

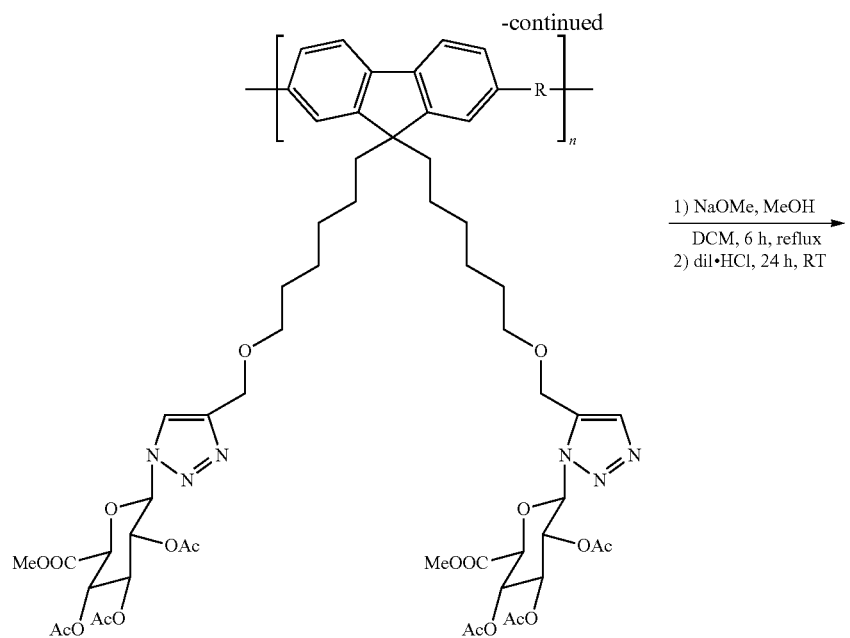
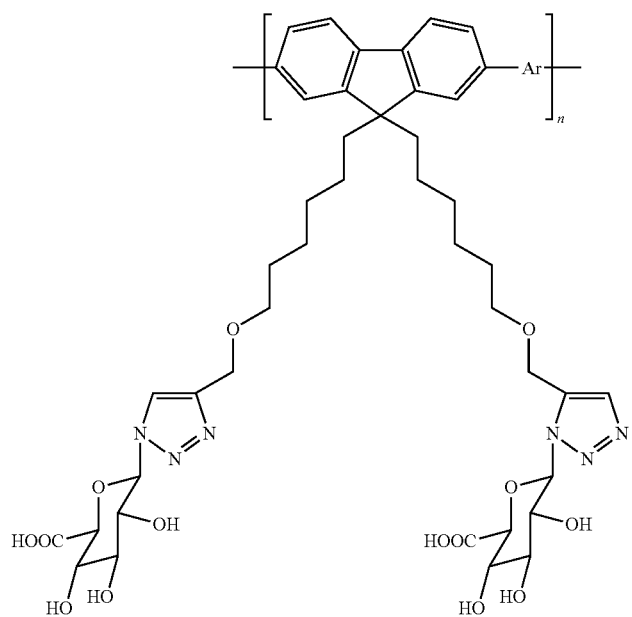
Reaction scheme for synthesis for PF-Ph-TEG is shown below:
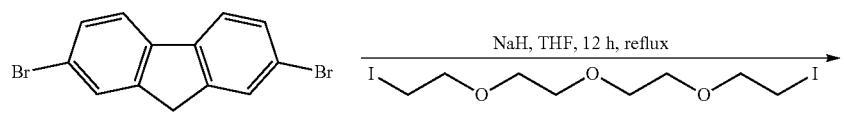

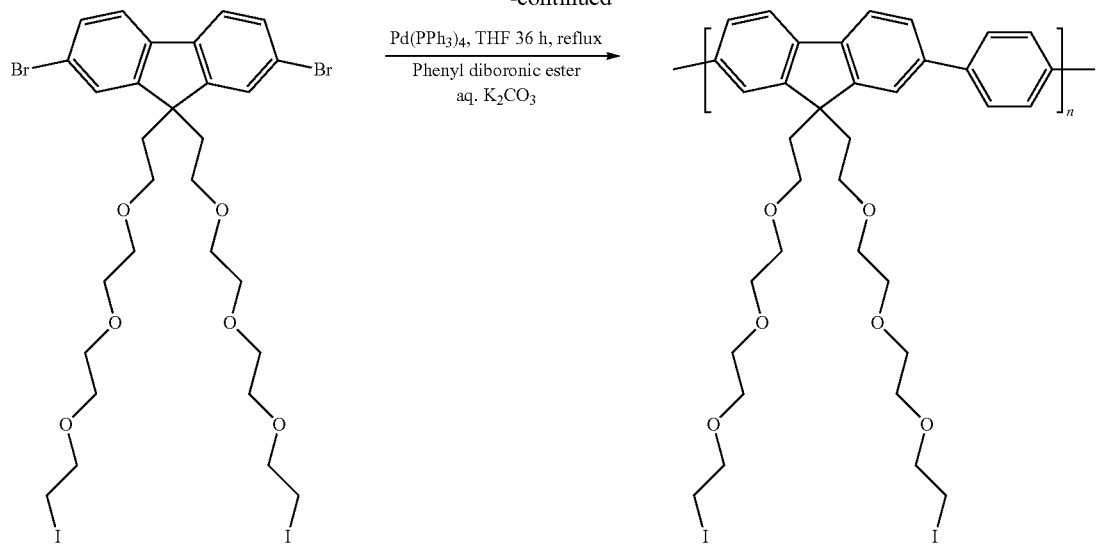
-continued

The invention is to detect free bilirubin in human serum samples. Normal and jaundiced patient samples can be differentiated by the present detection methods. The decrease in intensity of the emission color, measured at 420 nm, is an accurate measure of the bilirubin level in the sample.

The PF-Ph-Glu polymer shows a selective fluorescence quenching towards bilirurin not to biliverdin. The FIG. 9 clearly shows the percentage quenching of polymer fluorescence by bilirubin and there is no quenching from biliverdin. This is highly selective towards bilirubin compared to biliverdin. The concentration of analyte used is 10 μM. The polymer displayed clear selectivity towards bilirubin.

Figure 2:
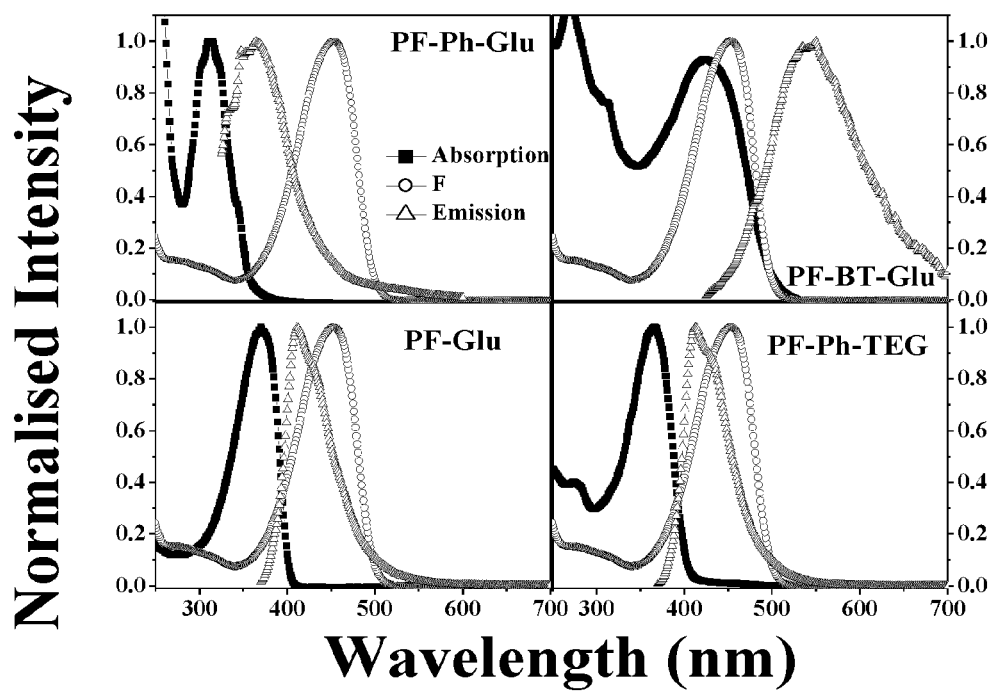
FIG. 2 shows absorption and emission properties of all polymers along with bilirubin absorption in water at pH=10.
Figure 11:
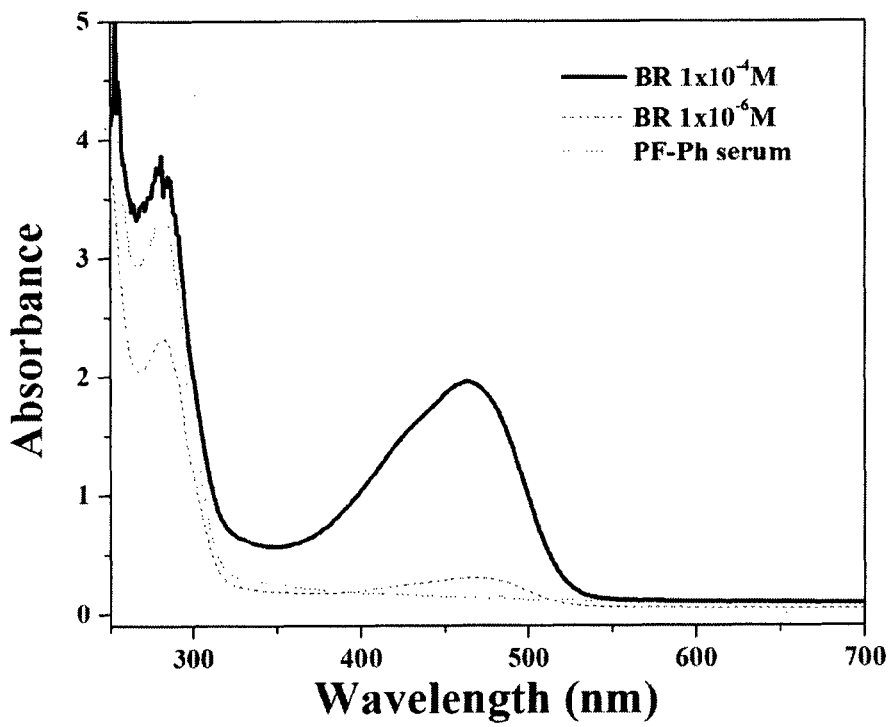
FIG. 11 Absorption spectrum PF-Ph-Glu polymer upon addition of various amounts of bilirubin in human serum samples.

The present invention describes sensing of bilirubin by fluorimetric method. The absorption and emission properties of the PF-Ph-Glu polymer alone as well as in presence of bilirubin in phosphate buffered saline at pH=10 are shown in FIG. 11, 12. The absorption and emission spectra of all polymers along with the absorption spectra of bilirubin is given in FIG. 2. The PF-BT-Glu polymer had a totally red shifted (540 nm) emission spectra compared to the other polymers due to the extended conjugation with benzathiadiazole units in the former. The emission of all polymers showed some extent of spectral overlap with bilirubin absorption.

Figure 4:
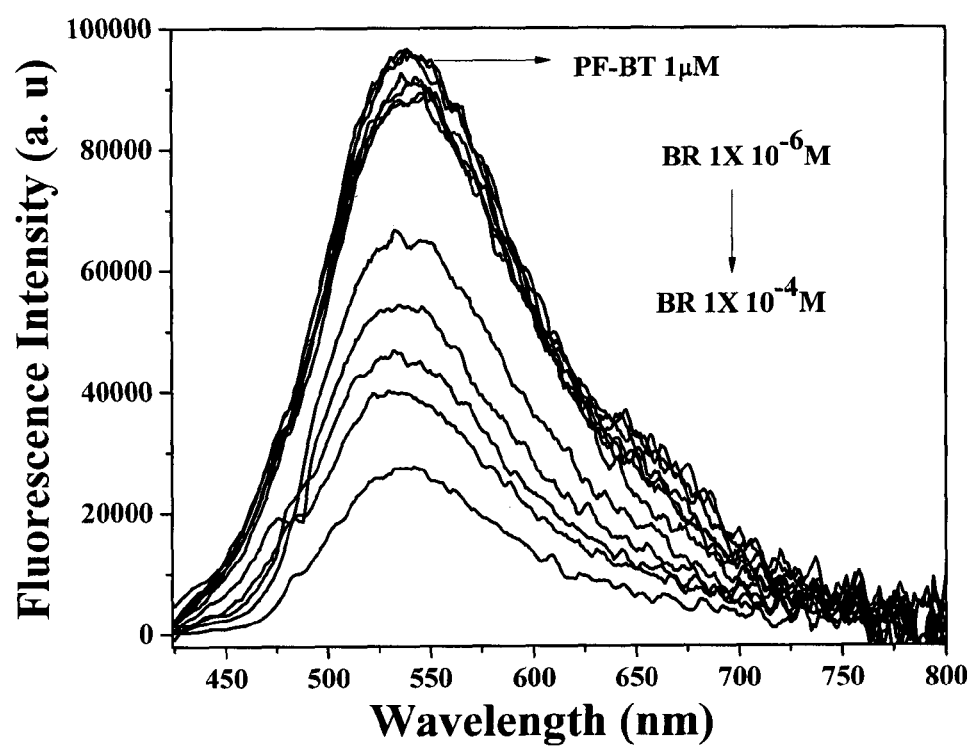
FIG. 4 shows the emission spectra of PF-BT-Glu polymer upon various additions of bilirubin (concentration range from $1\times10^{-6}$ M to $1\times10^{-4}$ M in PBS buffer at pH=10).
Figure 5:
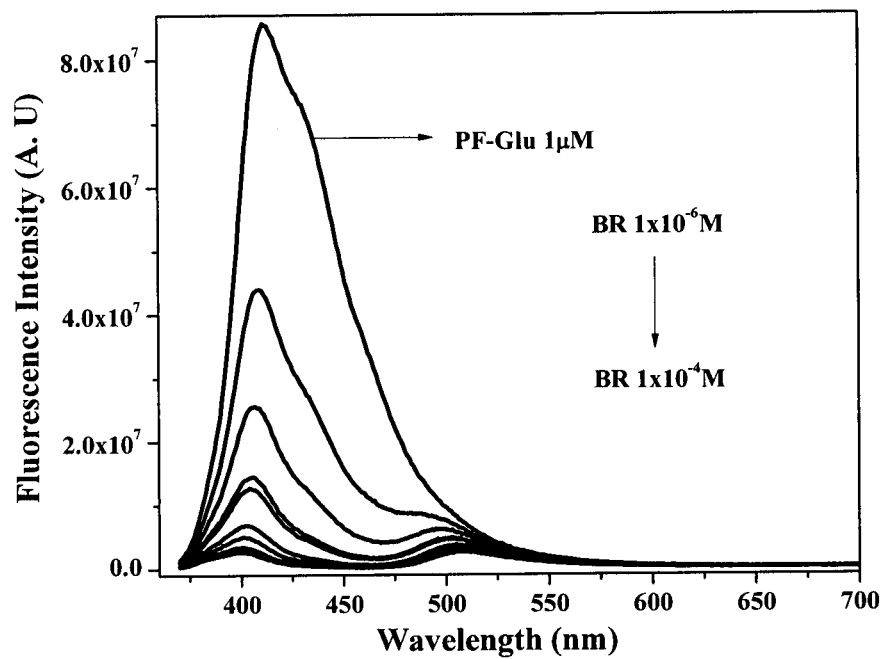
FIG. 5 shows Fluorescence quenching studies in Water for PF-Glu
Figure 6:
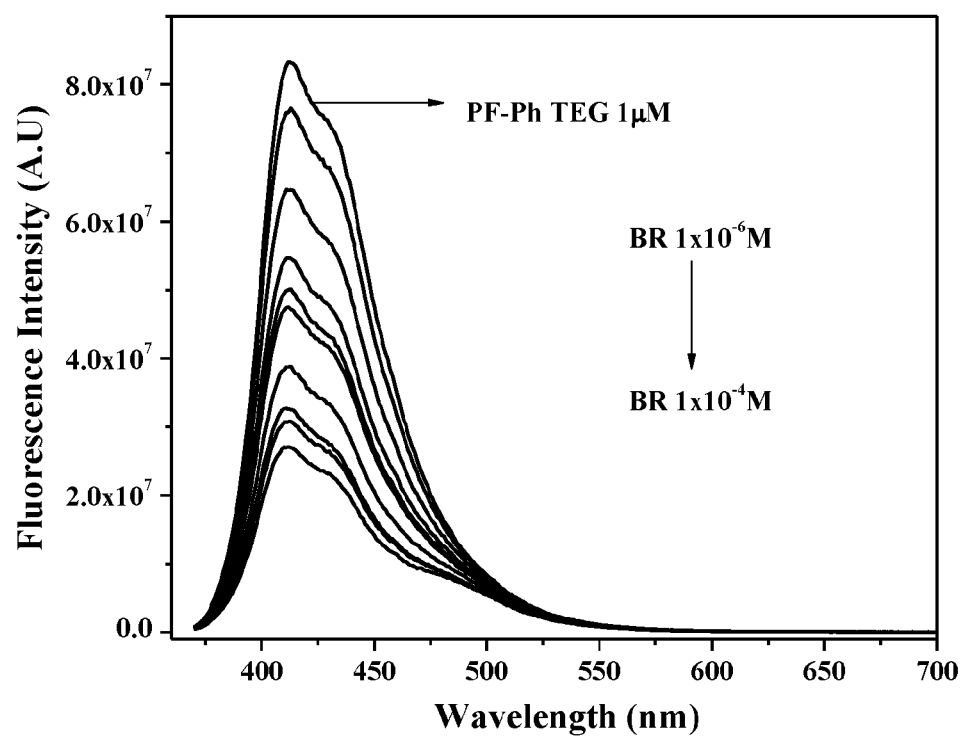
FIG. 6 shows Fluorescence quenching studies in DMF/Water for PF-Ph-TEG.
Figure 10:
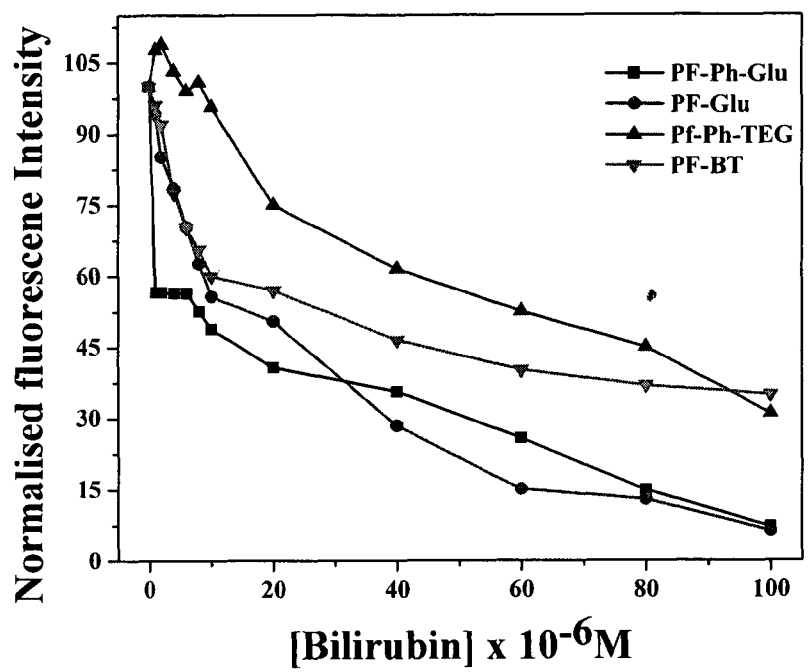
FIG. 10 Comparison plot of all polymers towards bilirubin quenching efficiency.

The emission spectra of PF-BT-Glu polymer upon various additions of bilirubin (concentration range from $1\times10^{-6}$ M to $1\times10^{-4}$ M in PBS buffer at pH=10) as shown in FIG. 4. The concentration of polymer was kept at $1\times10^{-6}$ M. The emission of polymer at 540 nm quenched upon addition of bilirubin; however, the extent of quenching of polymer fluorescence upon the first addition of bilirubin was not high and also the emission from bilirubin at 510 nm could not be distinguished since the polymer also emitted in the same region.

Gel permeation chromatography used to determine the molecular weight of the polymers using DMF as eluent and polystryrene as standard (FIG. 7). The values are tabulated in Table-1 and the chromatogram is given below.

TABLE 1

| Name | Mn | Mw | PDI |
| --- | --- | --- | --- |
| PF-Ph pro (DMF) | 20200 | 38300 | 1.89 |
| PF-BT pro(DMF) | 22900 | 57200 | 2.5 |
| PF-Glu pro(DMF) | 16800 | 25800 | 1.54 |
| PF-Ph depro (DMF) | 17900 | 35900 | 2.01 |
| PF-BT depro (DMF) | 20400 | 56700 | 2.78 |
| PF-Glu depro (DMF) | 15500 | 24200 | 1.56 |

The time correlated single photon counting (TCSPC) technique helps to identify or prove the concept of energy transfer. The decrease in lifetime of the polymer indicates the fluorescence quenching and occurrence of FRET. PF-Ph-Glu polymer in PBS buffer at pH=10 showed a lifetime of $\tau1=457$ ps and $\tau2=2.42$ ns with $\alpha1=0.87$ and $\alpha2=0.13$. Upon addition of bilirubin, the lifetime of the polymer decreased to $\tau1=21$ ps and $\tau2=2.56$ ns with $\alpha1=1$ and $\alpha2=0$ respectively (FIG. 8). The values are tabulated in Table-2. This result clearly indicated the quenching of fluorescence of PF-Ph-Glu due to energy transfer from polymer to bilirubin.

TABLE 2

| Sample | τ1 (ps) | τ2 (ns) | α1 | α2 | χ2 |
| --- | --- | --- | --- | --- | --- |
| PF-Ph | 457 | 2.42 | 0.87 | 0.13 | 1.24 |
| BR 1 × 10⁻⁶M | 439 | 2.29 | 0.87 | 0.13 | 1.25 |
| BR 2 × 10⁻⁶M | 247 | 1.12 | 0.89 | 0.11 | 1.003 |
| BR 4 × 10⁻⁶M | 148 | 1.09 | 0.89 | 0.11 | 1.005 |
| BR 6 × 10⁻⁶M | 37 | 1.14 | 0.92 | 0.08 | 1.008 |
| BR 8 × 10⁻⁶M | 21 | 2.56 | 1 | 0 | 1.012 |

EXAMPLES

Following examples are given by way of illustration and therefore should not be construed to limit the scope of the invention.

Example 1: Synthesis of 2, 7-dibromo-9, 9-(6-bromohexyl) fluorene

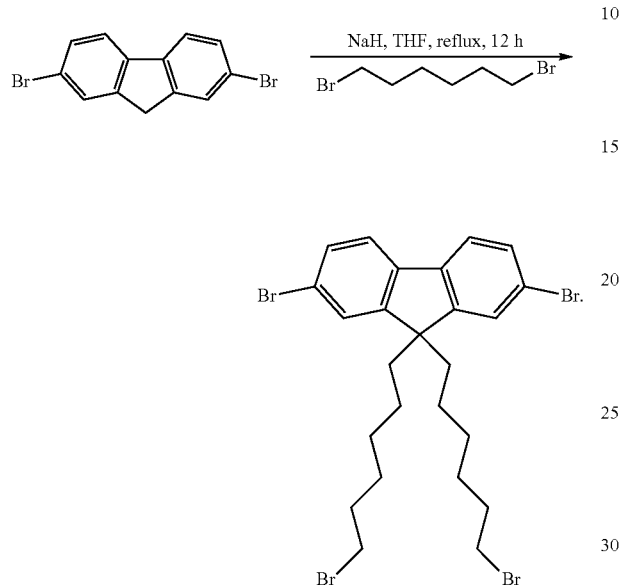

2, 7-dibromofluorene (3 g) and NaH (2.23 g) were taken in RB and purged with $N_2$. Dry THF (60 ml) was added to this reaction mixture. After a dark red coloured precipitate was observed, 1, 6-dibromohexane (8.94 g) was added and the reaction mixture were heated to reflux at 65° C. for 12 hrs. All the content was poured into water and extracted with ethyl acetate and washed with water, brine and finally solvent was evaporated under vacuum. The excess 1, 6-dibromohexane was distilled off. The crude compound was purified by column using pet ether as eluent. The product was obtained as yellow solid. Yield of the product is 80%. $^1$H NMR (200 MHz, $CDCl_3$): δ in ppm 7.54-7.42 (m, 6H), 3.28 (t, 4H), 1.96-1.87 (m, 4H), 1.73-1.64 (m, 4H), 1.26-1.03 (m, 8H), 0.65-0.57 (m, 4H). MALDI-TOF. Calculated=645.91; observed (M+2)=647.75.

Example 2: Synthesis of Propargyl Functionalized Fluorene

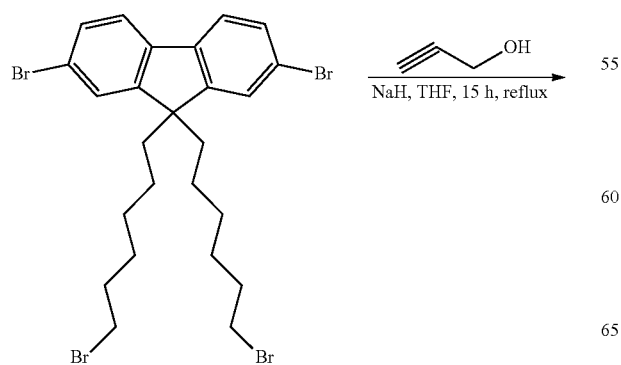

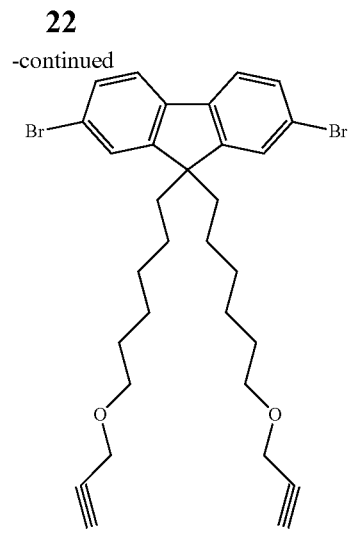

To a solution of NaH in dry THF, Propargyl alcohol was added dropwise and stirred for 30 minutes at room temperature. Then the 2, 7 dibromo-9, 9-(6-bromohexyl) fluorene was added slowly to the reaction mixture and the content was refluxed for 15 hrs. The reaction mixture was allowed to cool to room temperature and methanol was added to quench NaH. Then whole solution was evaporated and extracted with DCM; then the organic later was washed with water, brine and further purified by column chromatography using 97:3 pet ether:ethyl acetate as eluent. Yield is 60%. $^1$H NMR (200 MHz, $CDCl_3$): δ in ppm 7.54-7.36 (m, 6H), 4.07 (s, 2H), 3.28 (q, 4H), 2.38 (t, 4H), 1.96-1.87 (m, 4H), 1.73-1.64 (m, 4H), 1.26-1.03 (m, 8H), 0.65-0.57 (m, 4H). IR spectrum.v in cm-1 3308, 2978, 2865, 1648, 1500, 1250, 1135, 770.

Example 3: Acylation of Glucuronic Acid

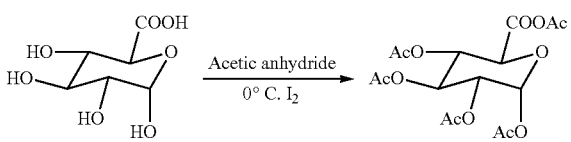

D-glucuroinc acid (1 g) was suspended in acetic anhydride (15 ml) and stirred at 0° C. $I_2$ (70 mg) was added slowly and the red solution was stirred for 2 hrs on ice and further 3 hrs at room temperature. For work up of reaction mixture, acetic anhydride was mostly removed in vacuum and the remaining mixture was extracted with DCM. The organic layer was then washed twice with $Na_2S_2O_3$ (1 M) dried, filtered and concentrated to afford acetylated glucuronic acid as white solid. The product was recrystallized from DCM/pet ether. $^1$H NMR (200 MHz, $CDCl_3$): δ in ppm 6.39 (d, 1H), 5.51 (s, 1H), 5.25 (s, 1H), 5.09 (dd, 1H), 4.46 (dd, 1H), 2.18 (s, 3H), 2.09 (s, 3H), 2.05 (s, 3H), 2.03 (s, 3H), 2.01 (s, 3H). Calculated −404.02; Observed M+Na −427.54.

Example 4: Synthesis of 1, 2, 3, 4-Tetra-O-Acetyl-methyl+D-Glucuronide

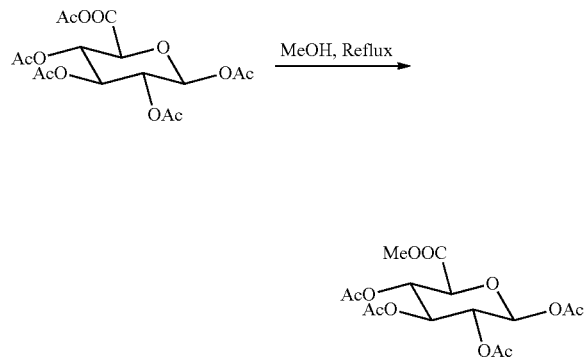

The pentacetate product was refluxed in dry methanol for 24 h. The excess methanol was distilled off and dried under vacuum. The product was purified by column chromatography using pet ether:ethyl acetate (4:6), and further recrystallized from methanol. Yield-65%. ¹H NMR (200 MHz, CDCl₃): δ in ppm 5.76 (d, 1H), 5.25 (q, 2H), 5.11 (t, 1H), 4.38 (d, 1H), 3.72 (s, 3H), 2.09 (s, 3H), 2.07 (s, 3H), 2.03 (s, 3H), 2.01 (s, 3H).

Example 5: Synthesis of 2, 3, 4-tri-O-acetyl-1-azido-1-deoxy-β-D-glucuronic acid methyl ester

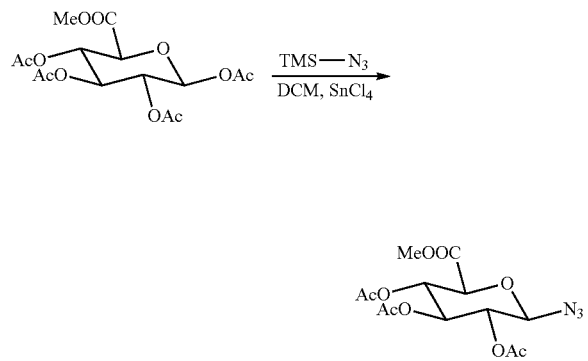

1, 2, 3, 4-Tetra-O-Acetyl-methyl-β-D-Glucuronide (5 g, 13.3 mmol) was dissolved anhydrous DCM (0.1 g/ml) under Ar atmosphere and add TMS-N₃ (4.4 ml, 33.3 mmol) and SnCl₄ (0.8 ml, 6.65 mmol). The reaction mixture was stirred for 15 h. The mixture was diluted with DCM and adds saturated sodium bicarbonate then solution was vigorously stirred for further 30 min. The mixture was poured into water and twice extracted with DCM. The combined organic layer was washed with 10% K₂CO₃, brine and finally with water. The final product was purified by column chromatography.

(EtOAc/MeOH=5/95). Yield −90%. ¹H NMR (200 MHz, CDCl₃): δ in ppm 5.24 (apt t, 2H), 4.95 (apt t, 1H), 4.72 (d, 1H), 4.13 (d, 1H), 3.77 (s, 3H), 2.07 (s, 3H), 2.03 (s, 3H), 2.01 (s, 3H). IR spectrum.ν in cm⁻¹ 3308, 2978, 2865, 1648, 1500, 1250, 1135, 770. LC-MS (Calculated −359.29; Observed M+Na −382.35).

Example 6: Click Reaction Between the Functionality

To a solution of azide in THF/MeOH/water (2:1:0.2) was added propargyl functionalized fluorene (1.5 eq) and the resultant reaction mixture was degassed by freeze-thaw cycles. CuSO₄ (0.2 eq) & sodium ascorbate was then added and the reaction was allowed to proceed for 24 hrs in Ar atmosphere. The progress of the reaction was monitored by IR. After completion of the reaction, solvent was removed by rotary evaporator. The reaction mixture was purified by column. ¹H NMR (200 MHz, CDCl₃): δ in ppm 9.41 (s, 2H), 7.41 (m, 10H), 5.46 (d, 1H), 4.09-3.87 (m, 10H), 3.73 (dd, 12H), 3.27 (t, 4H), 2.53 (t, 4H), 2.2-1.7 (s, 24H), 1.22 (t, 8H), 1.07 (q, 6H), 0.58 (t, 4H).

Example 7: Synthesis of glucuronic acid functionalized polymer (PF-Ph-GLUOAc)

(2R,3R,4R,5S,6R)-3,4,5-triacetoxy-6-(4-(((6-(2,7-di-bromo-9-(6-(((1-((2R,3R,4S,5S,6S)-3,4,5-triacetoxy-6-carboxytetrahydro-2H-pyran-2-yl)-1H-1,2,3-triazol-4-yl) methoxy)hexyl)-9H-fluoren-9-yl)hexyl)oxy) methyl)-1H-1, 2,3-triazol-1-yl)tetrahydro-2H-pyran-2-carboxylic acid (200 mg, 0.27 mmol), phenyl 1, 4-diboronic ester) (80 mg, 0.27 mmol) and tetrakis(triphenylphosphine) palladium (20 mg, 0.04 mmol) were taken in a two necked round bottom flask under nitrogen atmosphere. Dry THF (8 ml) was added to the mixture. K₂CO₃ dissolved in water (2 ml) was added to the reaction medium. The reaction mixture was heated to reflux for 36 hrs under nitrogen atmosphere. The mixture was cooled down to room temperature and added drop-wise into a stirred solution of methanol (100 ml) in an open vessel. The precipitate was isolated and dissolved in dichloromethane and filtered to remove the catalyst. The collected dichloromethane solution was concentrated under reduced pressure and purified by repeated precipitation from methanol (100 ml). The precipitate was filtered, washed with methanol (50 ml) and dried under high vacuum. ¹H NMR (200 MHz, CDCl₃): δ in ppm 9.41 (s, 2H), 7.76-7.41 (m, 10H), 5.46 (d, 1H), 4.09-3.87 (m, 10H), 3.73 (dd, 12H), 3.27 (t, 4H), 2.53 (t, 4H), 2.2-1.7 (s, 24H), 1.22 (t, 8H), 1.07 (q, 6H), 0.58 (t, 4ll).

Example 8: Synthesis of polyfluorene-alt-benzathiadiazole polymer

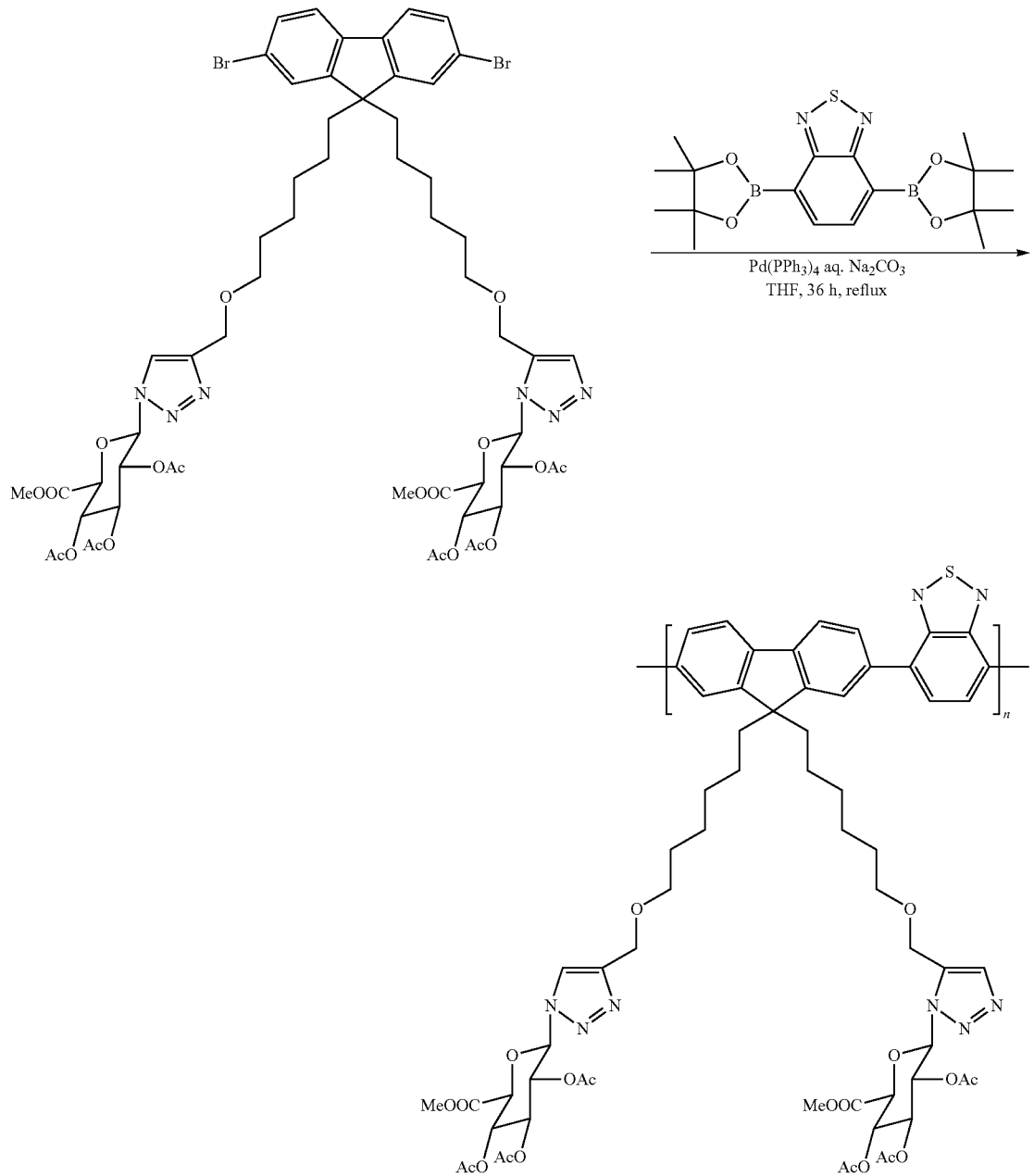

2-(5-(((6-(2,7-dibromo-9-(6-((1-((2R,3S,4S,5R,6S)-3,4,5-triacetoxy-6-(methoxycarbonyl) tetrahydro-2H-pyran-2-yl)-1H-1,2,3-triazol-4-yl)methoxy)hexyl)-9H-fluoren-9-yl) hexyl) oxy)methyl)-1H-1,2,3-triazol-1-yl)-6-(methoxycarbonyl)tetrahydro-2H-pyran-3,4,5-triyl triacetate (0.5 g, 0.27 mmol), 2,1,3-Benzothiadiazole-4,7-bis(boronic acid pinacol ester) (0.147 g, 0.338 mmol) and tetrakis(triphenylphosphine) palladium (40 mg, 0.04 mmol) were taken in a two necked round bottom flask under nitrogen atmosphere. Dry THF (8 ml) was added to the mixture. $K_2CO_3$ (0.21 g, 1.52 mmol) dissolved in water (2 ml) was added to the reaction medium. The reaction mixture was heated to reflux for 36 h under nitrogen atmosphere. The mixture was cooled down to room temperature and added drop-wise into a stirred solution of acetone (100 ml) in an open vessel. The precipitate was isolated and dissolved in dichloromethane and filtered to remove the catalyst. The collected dichloromethane solution was concentrated under reduced pressure and purified by repeated precipitation from acetone (100 ml). The precipitate was filtered, washed with acetone (50 ml) and dried under high vacuum. Yield: 80%.

$^1$H NMR (200 MHz, $CDCl_3$): δ in ppm 8.12 (dd, 2H), 7.37-7.19 (m, 6H), 5.76 (d, 2H), 5.28-5.16 (m, 411), 4.5 (dd, 2H), 4.16 (dd, 2H), 3.57 (s, 6H), 3.22 (t, 6H), 1.92, 1.89, 1.87 (s, 18H), 1.78-1.65 (m, 16H), 0.91 (b, 8H), 0.4 (b, 4H).

Example 9: Homopolymerization of glucuronic acid monomer (PF-glu)

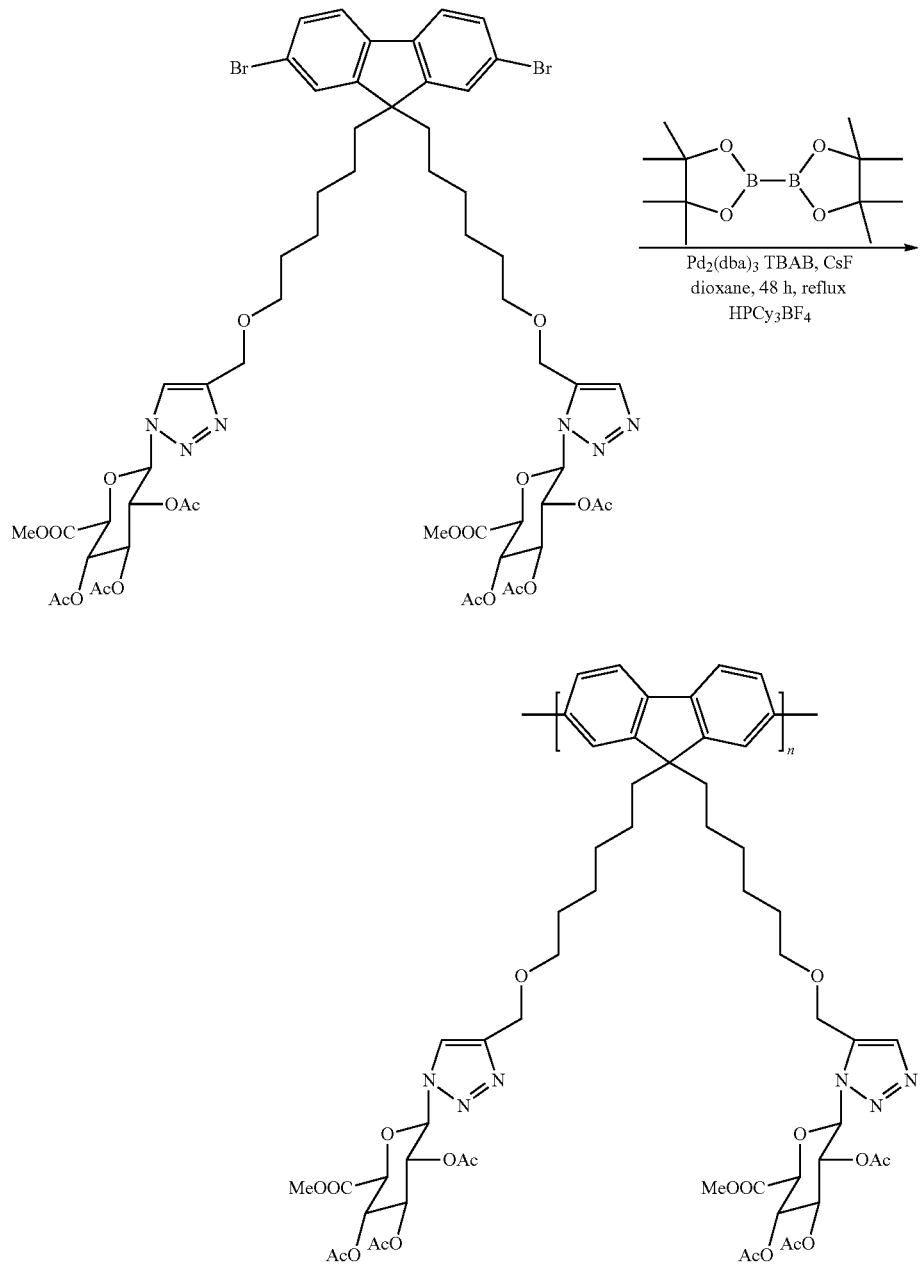

To a 50 ml round bottom flask, 2-(5-(((6-(2,7-dibromo-9-(6-((1-(((2R,3S,4S,5R,6S)-3,4,5-triacetoxy-6-(methoxycarbonyl)tetrahydro-2H-pyran-2-yl)-1H-1,2,3-triazol-4-yl)methoxy)hexyl)-9H-fluoren-9-yl)hexyl)oxy)methyl)-1H-1,2,3-triazol-1-yl)-6-(methoxycarbonyl)tetrahydro-2H-pyran-3,4,5-triyl triacetate (0.5 g, 0.379 mmol), was added along with bis(pinacolato)diboron (0.096 g, 0.379 mmol), Pd$_2$(dba)$_3$ (6.87 mg, 7.5 μmop, tricyclohexylphosphonium tetrafluoroborate (8.36 mg, 22.7 μmop, and CsF (0.4 g, 2.6 mmol). The RB was attached to a reflux condenser containing a septum punctured with a needle for argon/vacuum inlet. The flask was evacuated and backfilled with argon, after which degassed dioxane (35 ml) was transferred to the reaction mixture. The reaction was immersed in oil bath at 90° C. and stirred for 24 h at the same temperature. Tetrabutylammonium bromide (24.4 mg, 75 μmop dissolved in dry dioxane was added to the reaction mixture via syringe, and the reaction was stirred for 24 h. The reaction was cooled to room temperature, solvent removed in vacuum, and the contents redissolved in minimal amount of THF and precipitated in water. The solid was isolated by filtration, redissolved in THF and precipitated into acetone. Yield 85%. $^1$H NMR (200 MHz, CDCl$_3$): δ in ppm 7.37-7.19 (m, 6H), 5.76 (d, 2H), 5.28-5.16 (m, 4H), 4.5 (dd, 2H), 4.16 (dd, 2H), 3.57 (s, 6H), 3.22 (t, 6H), 1.92, 1.89, 1.87 (s, 18H), 1.78-1.65 (m, 16H), 0.91 (b, 8H), 0.4 (b, 4H).

Example 10: Post Modification to Give Water Soluble Polymer

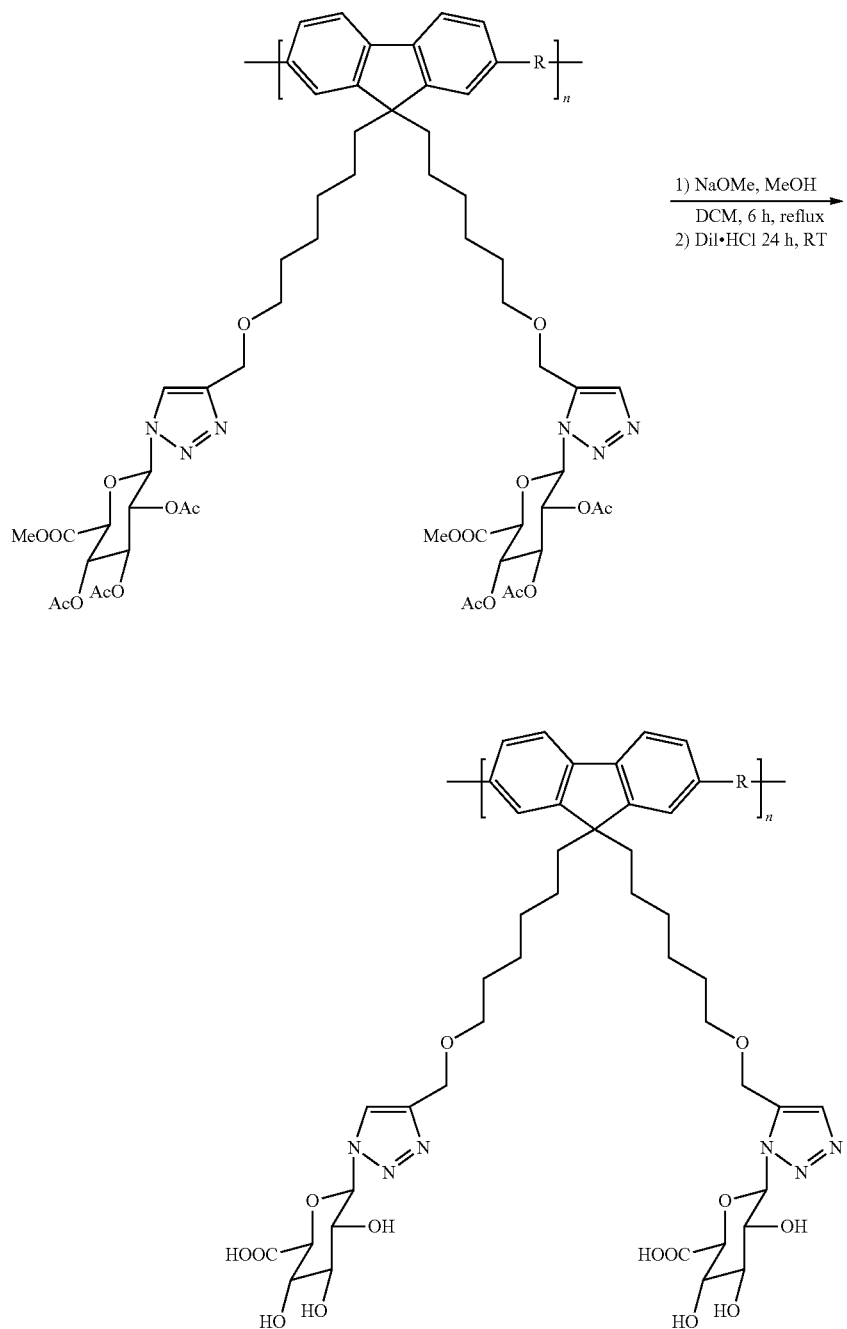

50 mg of the glucuronic acid functionalized polymer was taken in RB and dissolved in methanol (6 mL) and dichloromethane (10 mL), CH3ONa in methanol solution (3 mL, 1 M) was added. The mixture was stirred at room temperature for 6 hrs. After rotary evaporation of the solvents, the residue was washed with acetone, and dissolved in THF and water (1:1). Dilute HCl (0.5 M, 3 ml) was added and stirred for 24 h to hydrolyze the methyl ester. After removal of the solvent, DCM was added to remove unhydrolyzed polymer and then acetone was added. The precipitate was filtered and then dried under vacuum. Powders are redissolved in distilled water and dialyzed against Mill-Q water using 2 KDa molecular weight cut-off dialysis membrane for 2 days, changing the Mill-Q water every 6 hours. After freeze drying, pure polymer was obtained as yellow solid (yield=80%). $^1$H NMR (200 MHz, CDCl$_3$): δ in ppm 9.41 (s, 2H), 7.76-7.41 (m, 10H), 5.46 (d, 1H), 4.09-3.87 (m, 10H), 3.73 (dd, 12H), 3.27 (t, 4H), 2.53 (t, 4H), 1.22 (t, 8H), 1.07 (q, 6H), 0.58 (t, 4ll).

Example 11: Synthesis of Tetratethylene Glycol Monomer

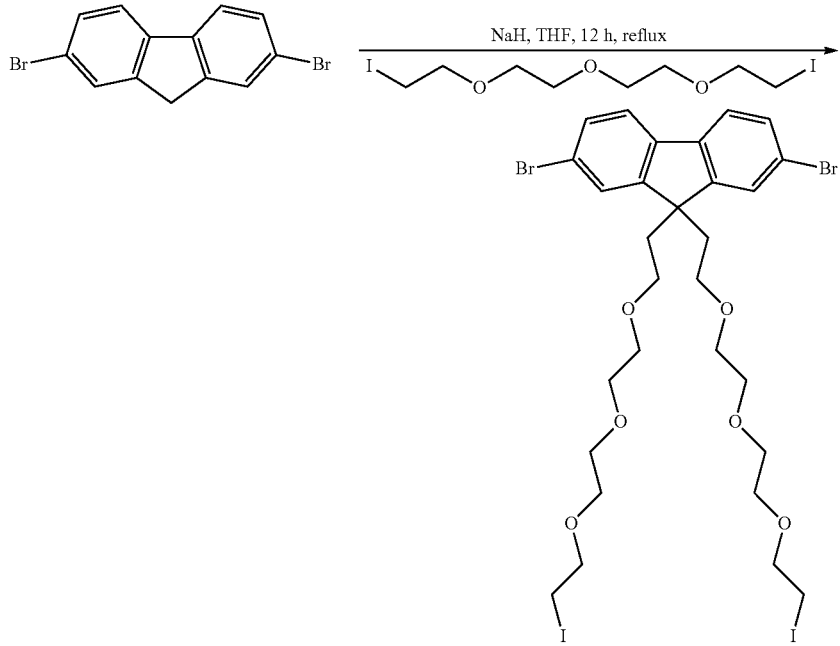

2, 7-dibromofluorene (3 g) and NaH (2.23 g) were taken in RB and purged with $N_2$. To this reaction mixture dry THF (60 ml) was added. After a dark red coloured precipitate was observed, 1-iodo-2-(2-(2-(2-iodoethoxy) ethoxy) ethoxy) ethane (18.94 g) was added and the reaction mixture was heated to reflux for 12 hrs. All the content was poured into water and extracted with ethyl acetate and washed with water, brine and finally solvent was evaporated under vacuum. The crude compound was purified by column using pet ether:ethylacetate (10:90) as eluent. The product was obtained as yellow liquid. Yield of the product is 85%. $^1$H NMR (200 MHz, $CDCl_3$): δ in ppm 7.55-7.44 (m, 6H), 4.15 (dd, 2H), 3.71 (m, 8H), 3.64-3.24 (dd, 6H), 3.12 (m, 4H), 2.23 (m, 4H), 2.05 (s, 2H), 1.27 (t, 4H).

Example 12: Synthesis of TEG functionalized polymer. (PF-Ph-TEG)

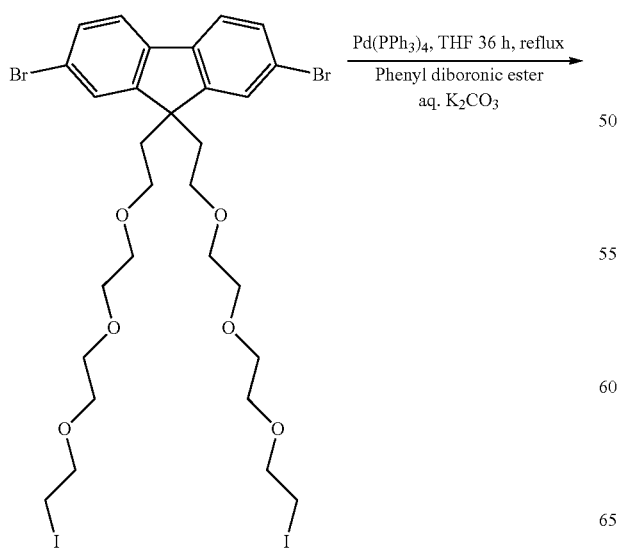

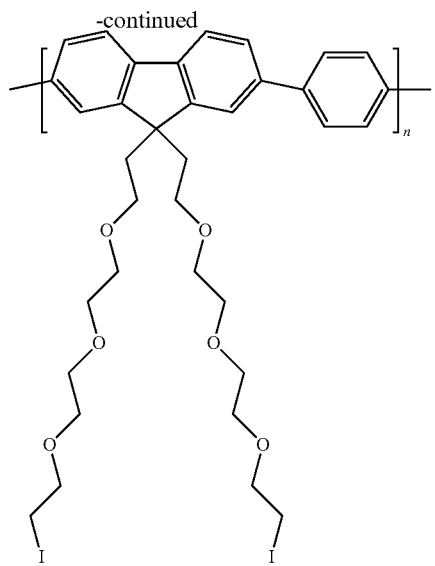

2, 7-dibromo-9, 9-bis (2-(2-(2-(2-iodoethoxy) ethoxy) ethoxy) ethyl)-9H-fluorene (500 mg, 0.56 mmol), phenyl 1,4-diboronic ester) (135 mg, 0.27 mmol) and tetrakis(triphenylphosphine) palladium (40 mg, 0.04 mmol) were taken in a two necked round bottom flask under nitrogen atmosphere. Dry THF (8 ml) was added to the mixture. $K_2CO_3$ dissolved in water (2 ml) was added to the reaction medium. The reaction mixture was heated to reflux for 36 h under nitrogen atmosphere. The mixture was cooled down to room temperature and added drop-wise into a stirred solution of methanol (100 ml) in an open vessel. The precipitate was isolated and dissolved in dichloromethane and filtered to remove the catalyst. The collected dichloromethane solution was concentrated under reduced pressure and purified by repeated precipitation from methanol (100 ml). The precipitate was filtered, washed with methanol (50 ml) and dried under high vacuum. $^1$H NMR (200 MHz, CDCl$_3$): δ in ppm 7.68-7.4 (m, 10H), 3.7-3.3 (b, 8H), 3.25-3.0 (dd, 6H), 2.74 (b, 4H), 2.29 (m, 4H), 2.0-1.6 (m, 12H), 1.23 (t, 4H).

Example 13: Fluorescence Sensing of Bilirubin by Polyfluorenes

Figure 3:
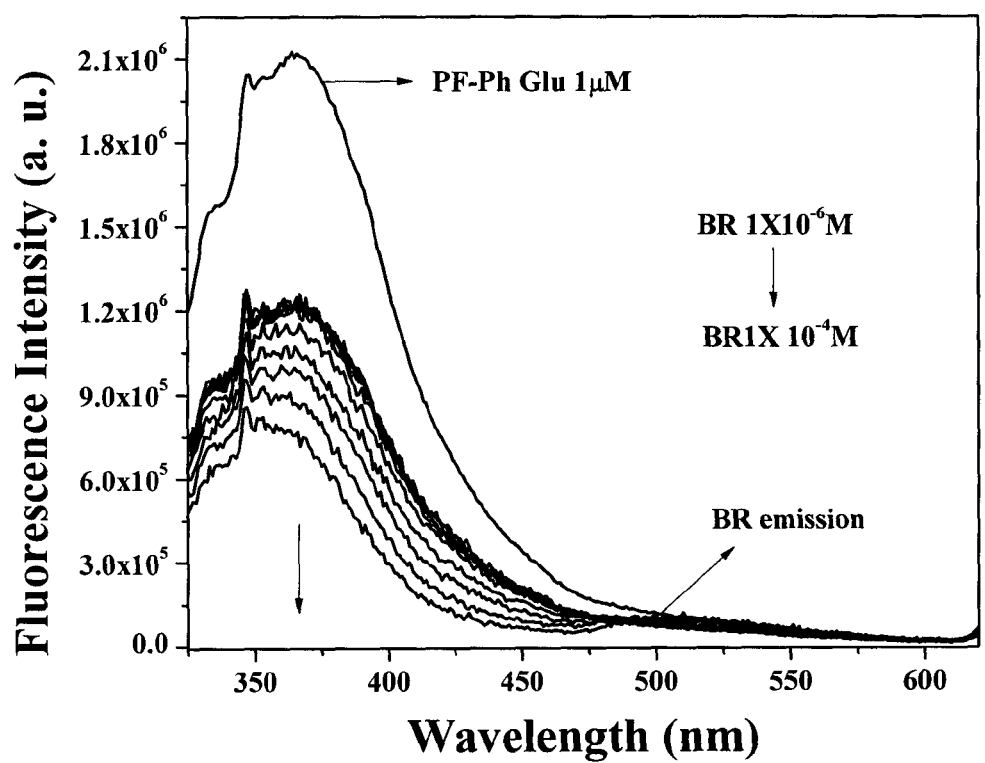
FIG. 3 shows corresponding emission spectra of polymer PF-Ph-Glu upon various additions of bilirubin.

Fluorescence sensing of bilirubin in water was done with the help of PF-Ph-GLU polymers. Bilirubin stock solution of $1\times10^{-6}$ M to $1\times10^{-4}$ M was prepared in water by the addition of 10 mM of NaOH. Fluorescence experiments were $1\times10^{-6}$ M polymer solution in distilled water. Since the PF-Ph-TEG polymer was not water soluble, the fluorescence experiments were conducted in DMF/Water (50:50). Only in the case of glucuronic acid functionalized polymer show a drastic quenching of fluorescence was observed with the appearance of FRET induced peak at 510 nm. Similarly fluorescence quenching experiment was done for PF-BT and homopolymers in water. The comparison plot was shown in FIG. 3 where PF-Ph-Glu clearly shows a drastic quenching at first addition and also fluorescence was completely quenched after addition of 100 μM of bilirubin. Other polymers did not show this much sensitivity and quenching.

Sensing Human Serum Samples

Polymer stock solution of 1 μM was prepared in PBS buffer at pH=10. Bilirubin stock solution of varying concentration from 1 μM to 100 μM was prepared in PBS buffer at pH=10. Human serum sample was used as received without any further purification.

Figure 12:
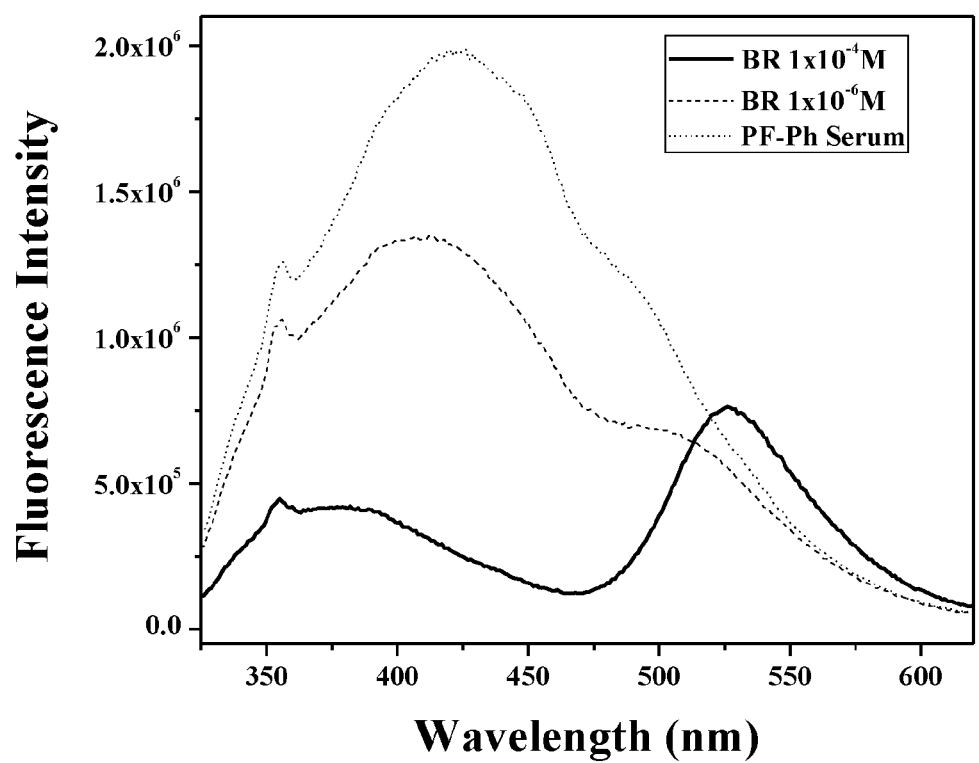
FIG. 12 Emission spectrum PF-Ph-Glu polymer upon addition of various amounts of bilirubin in human serum samples.

The sensing was done with total volume of 2.5 ml. The absorption and emission spectrum for serum sensing is given in FIGS. 11 and 12 respectively. The composition is as follows Polymer—1 ml Bilirubin—0.9 ml Serum—0.1 ml Buffer—0.5 ml A blank experiment was also done without the addition of bilirubin, but only 0.9 ml buffer and 0.1 ml serum was added. The blank sample gave an enhancement in the emission of polyfluorene. When bilirubin of different concentration was added a quenching of fluorescence of the polyfluorenes was observed.

Advantages of the Invention

The current invention deals with fluorimetric sensing of bilirubin by glucuronic acid functionalised polyfluorene. Fluorimetric method offers high selectivity because perfect energy match occurs only between the bilirubin and polyfluorene. Photophysical properties of polyfluorene will not match with biliverdin and other blood components, so other co analytes present in blood will not quench the fluorescence of polyfluorene. Fluorimetric method also displays high sensitivity because the polymer fluorescence can be perturbed by small amounts of analytes present. Another exciting advantage of this assay is the fact that it can measure both conjugated and unconjugated bilirubin with very short time of detection and also provide accurate method of detection over other methods.

We claim:

1. A compound of formula (I)

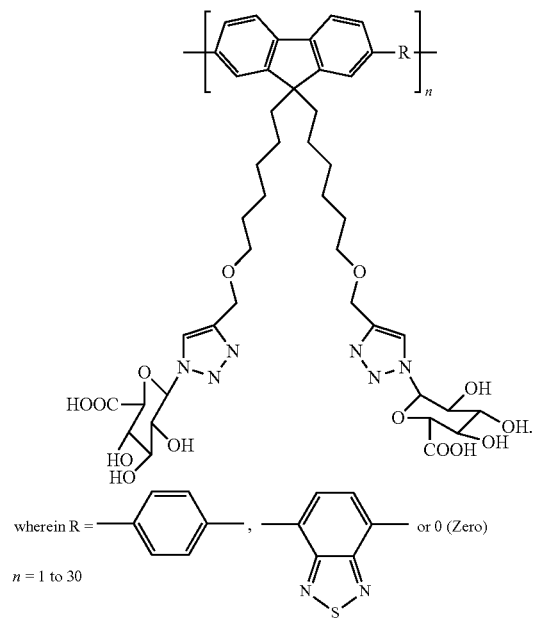

wherein R = [phenyl], [benzothiadiazole] or 0 (Zero)

n = 1 to 30

2. The compound as claimed in claim 1, wherein the compound is water soluble.

3. The compound as claimed in claim 1, wherein the compound is capable of sensing bilirubin in aqueous medium by fluorescence in the range of $1\times10^{-4}$ M to $1\times10^{-7}$ M.

4. The compound as claimed in claim 1, wherein the compound is capable of detecting bilirubin in human serum samples in the range from normal (<25 μmol/L~1.2 mg/dL) human bilirubin level to jaundiced bilirubin level (>50 μmol/L~2.5 mg/dL).[1]

5. A process for the preparation of compound as claimed in claim 1 comprising the steps of:
  a. refluxing the reaction mixture of 2, 7-diromofluorene and 1, 6-dibromo-hexane in presence of NaH in THF for period in the range of 10 to 12 hr followed by extraction to get 2, 7 dibromo-9, 9-(6-bromohexyl) fluorene;
  b. etherifying the 2, 7 dibromo-9, 9-(6-bromohexyl) fluorene as obtained in step (a) with propargyl alcohol to give 2, 7-dibromo-9, 9-bis (6-(prop-2-yn-1-yloxy) hexyl)-9H-fluorene;
  c. protecting D-Glucuronic acid with acetic anhydride to give penta acetylated product;
  d. refluxing the penta acetate product as obtained in step (c) with methanol to give 6-(methoxy-carbonyl) tetrahydro-2H-pyran-2, 3, 4, 5-tetrayl tetraacetate;
  e. reacting 6-(methoxy-carbonyl) tetrahydro-2H-pyran-2, 3, 4, 5-tetrayl tetraacetate as obtained in step (d) with TMS-N$_3$ and SnCl$_4$ followed by purification by column chromatography to obtain 2-azido-6-(methoxy-carbonyl) tetrahydro-2H-pyran-3,4,5-triyl triacetate;
  f. reacting compound of step (b) and compound of step (e) to get the sugar functionalized fluorene monomer;
  g. polymerizing the compound of step (f) by suzuki coupling to get glucuronic acid functionalized polyfluorene;

h. stirring the glucuronic acid functionalized polyfluorene in methanol and dichloromethane, CH3ONa in methanol solution at temperature in the range of 25 to 30° C. for period in the range of 5 to 6 hrs followed by hydrolyzing the ester using dilute HCl for period in the range of 20 to 24 h, purifying by dialysis to give water soluble compound of formula I.

6. The process as claimed in claim 5, wherein the suzuki coupling in step (g) is carried out by refluxing the monomer with phenyl 1, 4-diboronic ester in presence of $K_2CO_3$ and THF for 36 hrs under nitrogen atmosphere.

7. The process as claimed in claim 5, wherein the click reaction is carried out in step (f) for 24 hrs in argon atmosphere.

* * * * *